United States Patent
Larson et al.

(12)

(10) Patent No.: US 12,252,751 B2
(45) Date of Patent: *Mar. 18, 2025

(54) **METHODS OF DETECTING AND TYPING PATHOGENIC STRAINS OF *FRANCISELLA TULARENSIS***

(71) Applicant: Government of the United States as Represented by the Secretary of the Air Force, Wright-Patterson AFB, OH (US)

(72) Inventors: Marilynn A. Larson, Lincoln, NE (US); James C. Baldwin, Huber Heights, OH (US); Michael P. Dempsey, Bowie, MD (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 153 days.

This patent is subject to a terminal disclaimer.

(21) Appl. No.: 18/152,127

(22) Filed: Jan. 9, 2023

(65) Prior Publication Data

US 2023/0287520 A1 Sep. 14, 2023

Related U.S. Application Data

(63) Continuation of application No. 16/832,116, filed on Mar. 27, 2020, now Pat. No. 11,549,153, which is a continuation of application No. 15/908,808, filed on Feb. 28, 2018, now abandoned.

(60) Provisional application No. 62/464,666, filed on Feb. 28, 2017.

(51) Int. Cl.
| | | |
|---|---|---|
| C07H 21/04 | (2006.01) | |
| C12Q 1/68 | (2018.01) | |
| C12Q 1/689 | (2018.01) | |
| C12Q 1/6806 | (2018.01) | |
| C12Q 1/686 | (2018.01) | |

(52) U.S. Cl.
CPC ........... *C12Q 1/689* (2013.01); *C12Q 1/6806* (2013.01); *C12Q 1/686* (2013.01); *C12Q 2600/16* (2013.01)

(58) Field of Classification Search
None
See application file for complete search history.

(56) References Cited

U.S. PATENT DOCUMENTS 11,549,153 B2 * 1/2023 Larson ................... C12Q 1/689

OTHER PUBLICATIONS

Genbank Accession No. CP010115 (Year: 2015).*
J. Medical Microbiology, vol. 61, pp. 1535-1531, 2012 (Year: 2012).*
M. K. Gunnell et al., "A multiplex real-time PCR assay for the detection and differentiation of *Francisella tularensis* subspecies," J. Med. Microbiol., vol. 61 (2012) 1525-1531.

* cited by examiner

*Primary Examiner* — Jeanine A Goldberg
(74) *Attorney, Agent, or Firm* — AFMCLO/JAZ; James F. McBride

(57) ABSTRACT

A method of detecting a presence of *Francisella tularensis* (*F. tularensis*). The method includes amplifying a first nucleic acid from said specimen using a first plurality of primers, said first plurality of primers comprising SEQ ID NO 4 and SEQ ID NO 5. When the first nucleic acid is detected, then the presence of *F. tularensis* is determined.

7 Claims, 28 Drawing Sheets
Specification includes a Sequence Listing.

```
                    ┌─── 32
     34  NEGATIVE                    36
     ╱ CONTROL ASSAY ╲  YES    ┌──────────────┐
     ╲   PRODUCT     ╱───────▶│ CONTAMINANT  │
      ╲ OBSERVED?   ╱          │   PRESENT    │
           │                    └──────────────┘
           │ NO
           ▼
     38  POSITIVE                         NO BACTERIUM
     ╱ CONTROL ASSAY ╲  NO       ┌──────────────────┐
     ╲   PRODUCT     ╱──────────▶│ PRESENT OR       │── 40
      ╲ OBSERVED?   ╱             │ REACTION FAILED  │
           │                      └──────────────────┘
           │ YES                           │
           ▼                               ▼
      42 ┌─────────────┐                 ( END )
         │ PRESENCE OF A│
         │  BACTERIUM  │
         │  CONFIRMED  │
         └─────────────┘
                │
                ▼                                              46
     44  4Pan1 ASSAY       YES    ┌──────────────────────────────┐
     ╱   PRODUCT    ╲─────────────▶│ AT LEAST ONE STRAIN OF       │
     ╲  OBSERVED?   ╱              │ F. TULARENSIS IS PRESENT     │
           │                       └──────────────────────────────┘
           │ NO                                 │
           ▼                                    │ YES
     48 ┌─────────────┐                         ▼
        │ NO F.       │              50  3Pan1 ASSAY      YES
        │ TULARENSIS  │              ╱    PRODUCT    ╲──────┐
        │ IS PRESENT  │              ╲   OBSERVED?   ╱      │
        └─────────────┘                     │                │
                │                           │ NO             │
                ▼                           │                │
              ( END )                       │                │
                                            ▼                ▼
                          54 ┌──────────────────┐  52 ┌──────────────────┐
                             │ ONLY NONVIRULENT │     │ AT LEAST ONE     │
                             │ F. TULARENSIS    │     │ VIRULENT STRAIN OF│
                             │ SUBSPECIES NOVICIDA    │ F. TULARENSIS IS │
                             │ MUST BE PRESENT  │     │ PRESENT          │
                             └──────────────────┘     └──────────────────┘
                                     │                        │
                                     ▼                        ▼
                                    (A)                      (B)
```

```
                    ┌─────────┐         ↙─ 112
                    │  START  │
                    └────┬────┘
                         ▼              ┌─ 114
              ┌──────────────────────────┐
              │ REMOVE UNDESIRED SEQUENCES│
              └──────────────┬────────────┘
                             ▼           ┌─ 116
              ┌──────────────────────────┐
              │ RANDOMLY SAMPLE N SEQUENCES│
              │      TO FORM A SET        │
              └──────────────┬────────────┘
                             ▼
              ┌──────────────────────────┐
              │ COMPARE SEQUENCES IN THE SET │  118
              │  TO  F. TULARENSIS SEQUENCES │
              └──────────────┬────────────┘
```

FIG. 5

| S1 | X  |    |    |    |    |    | ENTROPY = 1 |
|----|----|----|----|----|----|----|-------------|
| S2 | X  | X  | X  |    |    |    | ENTROPY = 3 |
| S3 |    |    | X* |    | X* |    | ENTROPY = 2 |
| S4 |    |    |    |    |    | X  | ENTROPY = 1 |
| S5 |    |    |    | X  |    |    | ENTROPY = 1 |
|    | G1 | G2 | G3 | G4 | G5 | G6 |             |

```
                            SEQUENCE LISTING

Sequence total quantity: 33
SEQ ID NO: 1            moltype = DNA   length = 22
FEATURE                 Location/Qualifiers
source                  1..22
                        mol_type = other DNA
                        organism = Francisella tularensis
SEQUENCE: 1
tggagcatgt ggtttaattc ga                                            22

SEQ ID NO: 2            moltype = DNA   length = 19
FEATURE                 Location/Qualifiers
source                  1..19
                        mol_type = other DNA
                        organism = Francisella tularensis
SEQUENCE: 2
tgcgggactt aacccaaca                                                19

SEQ ID NO: 3            moltype = DNA   length = 23
FEATURE                 Location/Qualifiers
source                  1..23
                        mol_type = other DNA
                        organism = Francisella tularensis
SEQUENCE: 3
cacgagctga cgacarccrt gca                                           23

SEQ ID NO: 4            moltype = DNA   length = 24
FEATURE                 Location/Qualifiers
source                  1..24
                        mol_type = other DNA
                        organism = Francisella tularensis
SEQUENCE: 4
caycctagac tattctatac ttac                                          24

SEQ ID NO: 5            moltype = DNA   length = 27
FEATURE                 Location/Qualifiers
source                  1..27
                        mol_type = other DNA
                        organism = Francisella tularensis
SEQUENCE: 5
gtaaatctat ttacttgaaa catctgc                                       27

SEQ ID NO: 6            moltype = DNA   length = 26
FEATURE                 Location/Qualifiers
source                  1..26
                        mol_type = other DNA
                        organism = Francisella tularensis
SEQUENCE: 6
ccgtaccaag atcaaacaaa tatacc                                        26

SEQ ID NO: 7            moltype = DNA   length = 21
FEATURE                 Location/Qualifiers
source                  1..21
                        mol_type = other DNA
                        organism = Francisella tularensis
SEQUENCE: 7
tttacacccg tctccgttag t                                             21

SEQ ID NO: 8            moltype = DNA   length = 24
FEATURE                 Location/Qualifiers
source                  1..24
                        mol_type = other DNA
                        organism = Francisella tularensis
SEQUENCE: 8
ctcttaagga tgcaatttgg gatt                                          24

SEQ ID NO: 9            moltype = DNA   length = 29
FEATURE                 Location/Qualifiers
source                  1..29
                        mol_type = other DNA
                        organism = Francisella tularensis
```

```
SEQUENCE: 9
aagaggcaaa gctggaatta cactctctc                                    29

SEQ ID NO: 10           moltype = DNA   length = 21
FEATURE                 Location/Qualifiers
source                  1..21
                        mol_type = other DNA
                        organism = Francisella tularensis
SEQUENCE: 10
cacccagcaa caaagtagca c                                            21

SEQ ID NO: 11           moltype = DNA   length = 28
FEATURE                 Location/Qualifiers
source                  1..28
                        mol_type = other DNA
                        organism = Francisella tularensis
SEQUENCE: 11
ctatctcatc atcaaaatct ataagagc                                     28

SEQ ID NO: 12           moltype = DNA   length = 29
FEATURE                 Location/Qualifiers
source                  1..29
                        mol_type = other DNA
                        organism = Francisella tularensis
SEQUENCE: 12
ctcttgctgt tttttagct ggattatcc                                     29

SEQ ID NO: 13           moltype = DNA   length = 23
FEATURE                 Location/Qualifiers
source                  1..23
                        mol_type = other DNA
                        organism = Francisella tularensis
SEQUENCE: 13
ggctttgcta gcacaaataa acc                                          23

SEQ ID NO: 14           moltype = DNA   length = 26
FEATURE                 Location/Qualifiers
source                  1..26
                        mol_type = other DNA
                        organism = Francisella tularensis
SEQUENCE: 14
gataaacagc aattctttaa gacgac                                       26

SEQ ID NO: 15           moltype = DNA   length = 27
FEATURE                 Location/Qualifiers
source                  1..27
                        mol_type = other DNA
                        organism = Francisella tularensis
SEQUENCE: 15
cactgttagt gacaatccct gctatag                                      27

SEQ ID NO: 16           moltype = DNA   length = 23
FEATURE                 Location/Qualifiers
source                  1..23
                        mol_type = other DNA
                        organism = Francisella tularensis
SEQUENCE: 16
cctatccaat actccgagtt agt                                          23

SEQ ID NO: 17           moltype = DNA   length = 26
FEATURE                 Location/Qualifiers
source                  1..26
                        mol_type = other DNA
                        organism = Francisella tularensis
SEQUENCE: 17
aaatcaaaag aagagttaaa acaagc                                       26

SEQ ID NO: 18           moltype = DNA   length = 29
FEATURE                 Location/Qualifiers
source                  1..29
                        mol_type = other DNA
                        organism = Francisella tularensis
SEQUENCE: 18
ctctggccag ttatttttat caaagccag                                    29

SEQ ID NO: 19           moltype = DNA   length = 23
FEATURE                 Location/Qualifiers
source                  1..23
                        mol_type = other DNA
```

```
                              organism = Francisella tularensis
SEQUENCE: 19
agcacatgct agtttaatga gtt                                        23

SEQ ID NO: 20          moltype = DNA   length = 21
FEATURE                Location/Qualifiers
source                 1..21
                       mol_type = other DNA
                       organism = Francisella tularensis
SEQUENCE: 20
actagttgat gcagagttac c                                          21

SEQ ID NO: 21          moltype = DNA   length = 25
FEATURE                Location/Qualifiers
source                 1..25
                       mol_type = other DNA
                       organism = Francisella tularensis
SEQUENCE: 21
ctacacccat ttgggaaatg cctcc                                      25

SEQ ID NO: 22          moltype = DNA   length = 24
FEATURE                Location/Qualifiers
source                 1..24
                       mol_type = other DNA
                       organism = Francisella tularensis
SEQUENCE: 22
cttgttgtgg taaaaatagc ttag                                       24

SEQ ID NO: 23          moltype = DNA   length = 22
FEATURE                Location/Qualifiers
source                 1..22
                       mol_type = other DNA
                       organism = Francisella tularensis
SEQUENCE: 23
ggaagttttc atgagtaaga gc                                         22

SEQ ID NO: 24          moltype = DNA   length = 29
FEATURE                Location/Qualifiers
source                 1..29
                       mol_type = other DNA
                       organism = Francisella tularensis
SEQUENCE: 24
caataactgg cgcagcaaac ataccatac                                  29

SEQ ID NO: 25          moltype = DNA   length = 24
FEATURE                Location/Qualifiers
source                 1..24
                       mol_type = other DNA
                       organism = Francisella tularensis
SEQUENCE: 25
cttttctaaaa taaatgcagc tgct                                      24

SEQ ID NO: 26          moltype = DNA   length = 24
FEATURE                Location/Qualifiers
source                 1..24
                       mol_type = other DNA
                       organism = Francisella tularensis
SEQUENCE: 26
tcctatattt ctgatgctta tcag                                       24

SEQ ID NO: 27          moltype = DNA   length = 28
FEATURE                Location/Qualifiers
source                 1..28
                       mol_type = other DNA
                       organism = Francisella tularensis
SEQUENCE: 27
ccaccaattt cyccaccacc agcaaatc                                   28

SEQ ID NO: 28          moltype = DNA   length = 23
FEATURE                Location/Qualifiers
source                 1..23
                       mol_type = other DNA
                       organism = Francisella tularensis
SEQUENCE: 28
gatcagctcc tataaccatt ttc                                        23

SEQ ID NO: 29          moltype = DNA   length = 25
FEATURE                Location/Qualifiers
source                 1..25
```

```
                        mol_type = other DNA
                        organism = Francisella tularensis
SEQUENCE: 29
gcttaaagag ctactacaaa aaatc                                      25

SEQ ID NO: 30           moltype = DNA  length = 29
FEATURE                 Location/Qualifiers
source                  1..29
                        mol_type = other DNA
                        organism = Francisella tularensis
SEQUENCE: 30
aaggaacaat tccatcatca aacatatcc                                  29

SEQ ID NO: 31           moltype = DNA  length = 22
FEATURE                 Location/Qualifiers
source                  1..22
                        mol_type = other DNA
                        organism = Francisella tularensis
SEQUENCE: 31
gcaaaagaat agctatgaaa gc                                         22

SEQ ID NO: 32           moltype = DNA  length = 21
FEATURE                 Location/Qualifiers
source                  1..21
                        mol_type = other DNA
                        organism = Francisella tularensis
SEQUENCE: 32
ctcttgggta tagcagatat c                                          21

SEQ ID NO: 33           moltype = DNA  length = 27
FEATURE                 Location/Qualifiers
source                  1..27
                        mol_type = other DNA
                        organism = Francisella tularensis
SEQUENCE: 33
aatttcagca acaaccttat caacagc                                    27
```

METHODS OF DETECTING AND TYPING PATHOGENIC STRAINS OF *FRANCISELLA TULARENSIS*

This application is a continuation of U.S. application Ser. No. 16/832,116, filed Mar. 27, 2020 and issued as U.S. Pat. No. 11,549,153 on Jan. 10, 2023, which was a continuation of U.S. application Ser. No. 15/908,808 filed Feb. 28, 2018, which claimed the benefit of and priority to prior filed co-pending Provisional Application Ser. No. 62/464,666, filed Feb. 28, 2017. The specification of each of these applications is expressly incorporated herein by reference, each in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to the detection of infectious bacteria and, more particularly, to the detection of *Francisella tularensis*.

REFERENCE TO SEQUENCE LISTING

A Sequence Listing XML file is submitted wherewith, having a file name of "AFD-1490CON2 Sequence Listing," a creation date of May 26, 2023, and a size of 30.7 KB. The Sequence Listing XML file is a part of the specification and is incorporated herein by reference in its entirety.

BACKGROUND OF THE INVENTION

Tularemia is a zoonotic disease caused by a facultative intracellular pathogen, *Francisella tularensis* (hereafter, *F. tularensis*), that may be easily disseminated by a lethal dose of 10 organisms or less. As such, *F. tularensis* is a potential bioweapon able to cause a major health impact. *F. tularensis* is comprised of four subspecies: *tularensis* (type A), *holarctica* (type B), *mediasiatica*, and *novicida*. The type A subspecies is further separated into subtypes: A.I and A.II. These four subspecies and two subtypes differ considerably in virulence, with the type A.I clade possessing the greatest virulence and subspecies *novicida* possessing the least.

*F. tularensis* is distributed globally, with some stronger geographic associations, and can infect more species than any other known zoonotic pathogen. *F. tularensis* transmission occurs through oral, cutaneous, and conjunctival routes of exposure. Natural exposures to infected arthropods, animals, water, or food are common modes of infection. The most severe form of this disease is pneumonic tularemia that most likely results from the inhalation of contaminated (natural or man-made) aerosols. Fatality rates as high as 35% from a subtype A.I infection have been reported.

From a Public Health ("PH") and DoD Force Health Protection ("FHP") perspective, it is imperative to know if a potential exposure from a virulent *F. tularensis* strain, particularly a subtype A.I strain has occurred. However, all forms of tularemia, if untreated, can lead to hematogenous spread and eventual acute renal failure. While appropriate medical management is key for all exposures, rapid, accurate, and stand-alone identification of the *F. tularensis* subspecies and subtype is imperative to ensure that respiratory protection is considered when appropriate; however, this capability is currently lacking.

For example, the inability to subspeciate *F. tularensis* was observed in 2005 at a large gathering on the Capital Mall in Washington, DC. U.S. Government BioWatch sensors were triggered, and the Centers for Disease and Prevention ("CDC") issued a health advisory to healthcare personnel of possible tularemia exposure. Specimens obtained at the event were later analyzed and shown to contain signatures from *F. tularensis* subspecies *novicida*, a naturally-occurring, non-select agent that is not virulent. Had the subspecies been identified prospectively on-site, the CDC health advisory would have been unnecessary.

A number of other related, avirulent bacterial strains further complicate the positive identification of *F. tularensis*, such as *Francisella persica* (a nonpathogenic tick endosymbiont formally classified as *Wolbachia persica*).

Conventional polymerase chain reaction ("PCR") assays do not offer accurate subspecies and subtype differentiation. These methods are also not able to definitively identify all four subspecies of *F. tularensis* with sufficient simplicity that identification may be done in or near the point of operations. Research and reference laboratory methods and platforms capable of *F. tularensis* subspeciation are known, but require a complex scoring matrix and are only able to differentiate three of the four *F. tularensis* subspecies.

Thus there remains a need for rapid, portable, and accurate stand-alone detection assays that can differentiate all four *F. tularensis* subspecies and the two type-A subtypes. Such assays should be suitable for deployment in Joint Biological Agent Identification and Diagnostic System ("JBAIDS"), or for next generation platforms (such as sequencing or dense array PCR) that will eventually replace JBAIDS.

SUMMARY OF THE INVENTION

The present invention overcomes the foregoing problems and other shortcomings, drawbacks, and challenges of rapidly and accurately detecting and differentiating all four *F. tularensis* subspecies and subtypes using deployable supplies and instruments. While the invention will be described in connection with certain embodiments, it will be understood that the invention is not limited to these embodiments. To the contrary, this invention includes all alternatives, modifications, and equivalents as may be included within the spirit and scope of the present invention.

According to embodiments of the present invention, a method of detecting a presence of *Francisella tularensis* (*F. tularensis*) or nucleic acids thereof includes amplifying a first nucleic acid from said specimen using a first plurality of primers, said first plurality of primers comprising SEQ ID NO 4 and SEQ ID NO 5. When the first nucleic acid is detected, then the presence of *F. tularensis* or nucleic acids thereof is determined.

In some aspects of the present invention, a detection assay for detecting the presence of *F. tularensis* includes a first plurality of primers comprising SEQ ID NO 4 and SEQ ID NO 5.

Other embodiments of the present invention include a method of detecting a virulent strain of *F. tularensis* or nucleic acids thereof by amplifying a first nucleic acid from said specimen using a first plurality of primers, said first plurality of primers comprising SEQ ID NO 7, and SEQ ID NO 8. When the first nucleic acid is detected by using a first probe comprising SEQ ID NO 9, then the presence of a virulent strain of *F. tularensis* or nucleic acids thereof is determined.

For some aspects of the present invention, a detection assay for detecting the presence of a virulent strain of *F. tularensis* includes a first plurality of primers comprising SEQ ID NO 7 and SEQ ID NO 8. The assay further includes a first probe comprising a fluorescent reporter dye coupled to an initial 5'-nucleotide of SEQ ID NO 9.

Yet other embodiments of the present invention include a method of detecting a non-virulent strain of *F. tularensis* (e.g., subsp. *novicida*) or nucleic acids thereof by amplifying a first nucleic acid from said specimen using a first plurality of primers and detecting the first nucleic acid using a first probe. The first plurality of primers and corresponding first probe may be selected from the group consisting of SEQ ID NO 22, SEQ ID NO 23, and SEQ ID NO 24; SEQ ID NO 25, SEQ ID NO 26, and SEQ ID NO 27; SEQ ID NO 28, SEQ ID NO 29, and SEQ ID NO 30; and SEQ ID NO 31, SEQ ID NO 32, and SEQ ID NO 33. Detection of the first nucleic acid determines the presence of the non-virulent strain of *F. tularensis* (e.g., subsp. *novicida*) or nucleic acids thereof.

Some aspects of the present invention include a detection assay for detecting the presence of a non-virulent strain of *F. tularensis* (e.g., subsp. *novicida*) or nucleic acids thereof. The assay includes a first plurality of primers and a first probe selected from the group consisting of SEQ ID NO 22, SEQ ID NO 23, and SEQ ID NO 24; SEQ ID NO 25, SEQ ID NO 26, and SEQ ID NO 27; SEQ ID NO 28, SEQ ID NO 29, and SEQ ID NO 30; and SEQ ID NO 31, SEQ ID NO 32, and SEQ ID NO 33. A fluorescent reporter dye is coupled to an initial 5'-nucleotide of the first probe.

According to embodiments of the present invention, a method of detecting a virulent strain of *F. tularensis*, subspecies *tularensis* or nucleic acids thereof in a specimen by amplifying a first nucleic acid from said specimen using a first plurality of primers and detecting the first nucleic acid using a first probe. The first plurality of primers and corresponding first probe may be selected from the group consisting of SEQ ID NO 10, SEQ ID NO 11, and SEQ ID NO 12; and SEQ ID NO 13, SEQ ID NO 14, and SEQ ID NO 15. Detection of the first nucleic acid determines the presence of the subspecies *tularensis* (type A) or nucleic acids thereof.

In aspects of the present invention, a detection assay for detecting the presence *F. tularensis*, subspecies *tularensis* (type A) or nucleic acids thereof. The assay includes a first plurality of primers and a first probe selected from the group consisting of SEQ ID NO 10, SEQ ID NO 11, and SEQ ID NO 12; and SEQ ID NO 13, SEQ ID NO 14, and SEQ ID NO 15. A fluorescent reporter dye is coupled to an initial 5'-nucleotide of the first probe.

Other embodiments of the present invention are directed to a method of detecting and distinguishing *F. tularensis*, subspecies *tularensis*, subtypes A.I or nucleic acids thereof and *F. tularensis*, subspecies *tularensis*, A.II in a specimen or nucleic acids thereof. The method includes amplifying a first nucleic acid from said specimen using a first plurality of primers comprising SEQ ID NO 10 and SEQ ID NO 11 and amplifying a second nucleic acid from said specimen using a second plurality of primers comprising SEQ ID NO 13 and SEQ ID NO 14. The first nucleic acid is detected using a first probe comprising SEQ ID NO 12; the second nucleic acid is detected using a second probe comprising SEQ ID NO 15. Detection of the first nucleic acid indicates a presence of *F. tularensis*, subspecies *tularensis*, subtype A.I. in the specimen; detection of the second nucleic acid indicates the presence of *F. tularensis*, subspecies *tularensis*, subtype A.II. in the specimen.

Yet other embodiments of the present invention include a method of detecting a presence of *F. tularensis*, subspecies *holarctica* or nucleic acids thereof in a specimen by amplifying a first nucleic acid using a first plurality of primers comprising SEQ ID NO 16 and SEQ ID NO 17. When the first nucleic acid is detected using a first probe comprising SEQ ID NO 18, then the presence of *F. tularensis*, subspecies *holarctica* or nucleic acids thereof is determined.

For some aspects of the present invention, a detection assay kit for detecting a presence of *F. tularensis*, subspecies *holarctica* or nucleic acids thereof in a specimen includes a first plurality of primers comprising SEQ ID NO 16 and SEQ ID NO 17. The assay kit further includes a first probe comprising a fluorescent reporter dye coupled to an initial 5'-nucleotide of SEQ ID NO 18.

Still other embodiments of the present invention include a method of detecting *F. tularensis*, subspecies *mediasiatica* or nucleic acid thereof in a specimen by amplifying a first nucleic acid from said specimen using a first plurality of primers comprising SEQ ID NO 19, and SEQ ID NO 20. When the first nucleic acid is detected using a first probe comprising SEQ ID NO 21, then the presence of *F. tularensis*, subspecies *mediasiatica* or nucleic acid thereof is determined.

For some aspects of the present invention, a detection assay kit for detecting a presence of *F. tularensis*, subspecies *mediasiatica* or a nucleic acid thereof in a specimen includes a first plurality of primers comprising SEQ ID NO 19 and SEQ ID NO 20. The assay kit further includes a first probe comprising a fluorescent reporter dye coupled to an initial 5'-nucleotide of SEQ ID NO 21.

Other aspects of the present invention include a detection assay kit for detecting *F. tularensis* or a nucleic acid thereof. The assay kit includes a first assay, a second assay, a third assay, a fourth assay, a fifth assay, a sixth assay, a seventh assay, an eighth assay, a ninth assay, a and a tenth assay. The first assay includes a first plurality of primers comprising SEQ ID NO 4 and SEQ ID NO 5 and a first probe comprising a fluorescent reporter dye coupled to an initial 5'-nucleotide of SEQ ID NO 6. The second assay includes a second plurality of primers comprising SEQ ID NO 7 and SEQ ID NO 8 and a second probe comprising a fluorescent reporter dye coupled to an initial 5'-nucleotide of SEQ ID NO 9. The third assay includes a third plurality of primers comprising SEQ ID NO 10 and SEQ ID NO 11 and a third probe comprising a fluorescent reporter dye coupled to an initial 5'-nucleotide of SEQ ID NO 12. The fourth assay includes a fourth plurality of primers comprising SEQ ID NO 13 and SEQ ID NO 14 and a fourth probe comprising a fluorescent reporter dye coupled to an initial 5'-nucleotide of SEQ ID NO 15. The fifth assay includes a fifth plurality of primers comprising SEQ ID NO 16 and SEQ ID NO 17 and a fifth probe comprising a fluorescent reporter dye coupled to an initial 5'-nucleotide of SEQ ID NO 18. The sixth assay includes a sixth plurality of primers comprising SEQ ID NO 19 and SEQ ID NO 20 and a sixth probe comprising a fluorescent reporter dye coupled to an initial 5'-nucleotide of SEQ ID NO 21. The seventh assay includes a seventh plurality of primers comprising SEQ ID NO 22 and SEQ ID NO 23 and a seventh probe comprising a fluorescent reporter dye coupled to an initial 5'-nucleotide of SEQ ID NO 24. The eighth assay includes an eighth plurality of primers comprising SEQ ID NO 25 and SEQ ID NO 26 and an eighth probe comprising a fluorescent reporter dye coupled to an initial 5'-nucleotide of SEQ ID NO 27. The ninth assay includes a ninth plurality of primers comprising SEQ ID NO 28 and SEQ ID NO 29 and a ninth probe comprising a fluorescent reporter dye coupled to an initial 5'-nucleotide of SEQ ID NO 30. The tenth assay includes a tenth plurality of primers comprising SEQ ID NO 31 and SEQ ID NO 32 and a tenth probe comprising a fluorescent reporter dye coupled to an initial 5'-nucleotide of SEQ ID NO 33.

According to still other embodiments of the present invention, a method of detecting a presence of the non-virulent subspecies, specifically *Francisella tularensis* (*F. tularensis*) subsp. *novicida* or *F. tularensis* subsp. *novicida* nucleic acid in a specimen includes amplifying a first nucleic acid from said specimen using a first plurality of primers, said first plurality of primers comprising SEQ ID NO 22, SEQ ID NO 23; SEQ ID NO 25, SEQ ID NO 26; SEQ ID NO 28, SEQ ID NO 29; SEQ ID NO 31, and SEQ ID NO 32. The first nucleic acid is detected using a first probe comprising SEQ ID NO 24; SEQ ID NO 27; SEQ ID NO 30; and SEQ ID NO 33. Detection indicates the presence of *F. tularensis* subsp. *novicida* or *F. tularensis* subsp. *novicida* nucleic acid in the specimen.

Other variations of the present invention include the use of direct DNA sequencing of the PCR products, using some or all of the sequences described in this invention. Sequencing may allow for the measurement of the quantitative and quadrative properties of the product and the additional sequence information may improve both the throughput and accuracy of qPCR based singleplex or multiplex measurements Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 1-5 are flowcharts illustrating a method of detecting a *F. tularensis* species, a subspecies thereof, a subtype thereof, or a combination thereof according to an embodiment of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

The assays according to embodiments of the present invention comprise a plurality of primers, probes, and assay conditions that provide *F. tularensis* species-, subspecies-, and subtype-level differentiation via PCR. The various embodiments may be singleplex qPCR (real time PCR, "qPCR," wherein such methods are similar except as specifically noted) assays or multiplex qPCR assays with sequencing to detect multiple *F. tularensis* targets. The singleplex qPCR assay embodiments detect each *F. tularensis* target separately; in the multiplexed qPCR assay embodiments, different targets may be multiplexed in a single tube. The qPCR assays, according to embodiments of the present invention, are operable on the currently fielded DoD JBAIDS (BioFire Defense, Salt Lake City, UT), the APPLIED BIOSYSTEMS 7500 Fast instrument (Thermo Fisher Scientific, Waltham, MA), the 3M Integrated Cycler (Focus Diagnostics of Diasorin Molecular, LLC, Cypress, California), as well as most other real-time PCR instruments. Furthermore, assays according to embodiments of the present invention may be operated by PCR amplification followed by DNA sequence-based genotyping that is compatible on most DNA sequencers, such as but not limited to, the Ion Torrent (Thermo Fisher, formerly Life Technologies, Corp.). Each assay variant is independently capable of identifying and subspeciating *F. tularensis* to guide and promote the appropriate public health, Force Health Protection, family health public, medical response, or a combination of one of more of these.

The assays according to embodiments of the present invention detect the qualitatively amplicon exact sequences rather than relying on detection via fluorescent signal with a probe or observing amplicon presence. According to some embodiments, mere detection of a certain qualitative product by sequence is sufficient to be diagnostic for a given *F. tularensis* subspecies or subtype. The non-specific detector embodiments (those that make amplicon from more than one strain) contain numerous single nucleotide polymorphisms ("SNP") that are indicative of *F. tularensis* subspecies.

Figure 1:
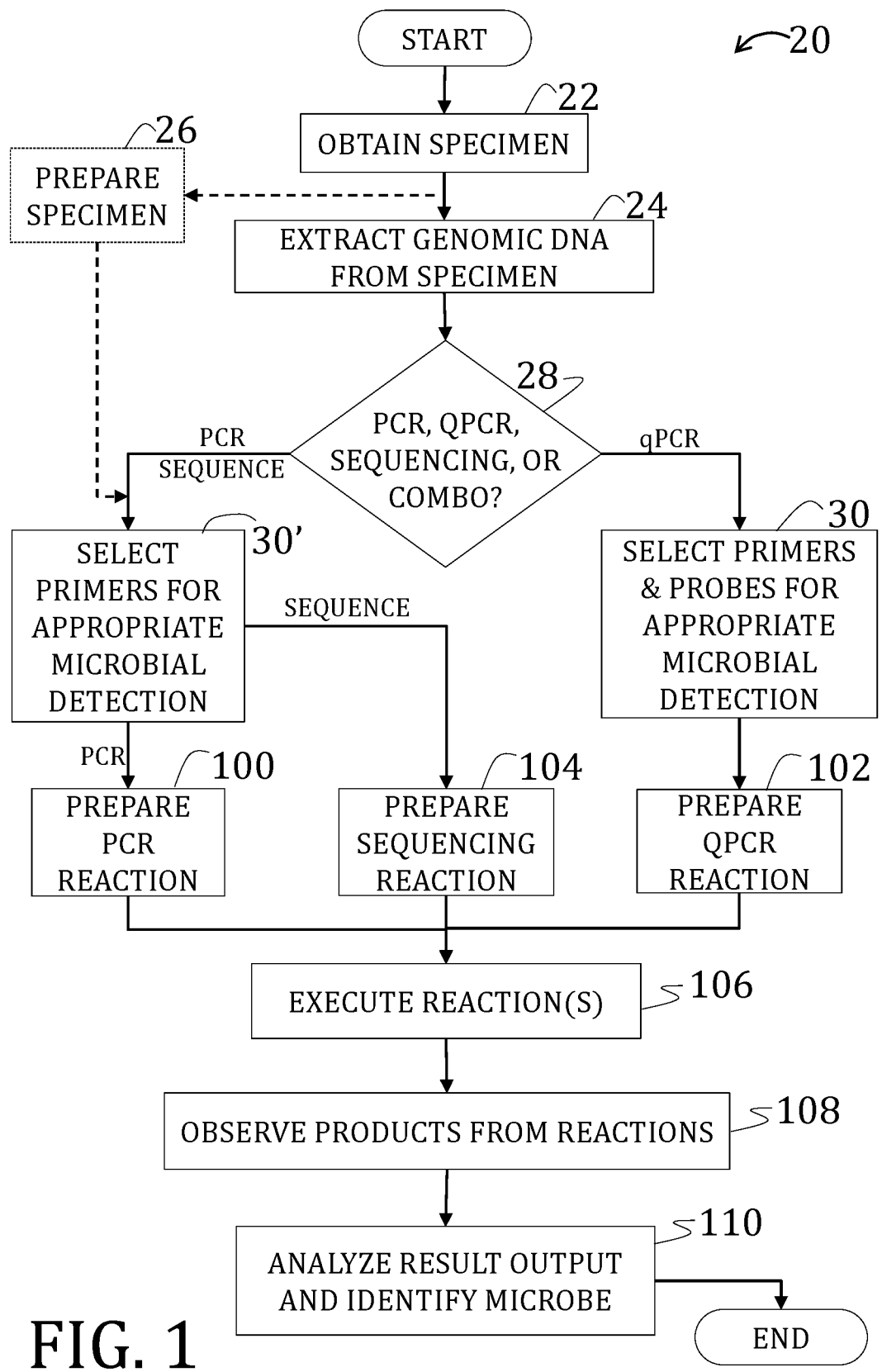

Referring now to the figures, and in particular to FIG. 1, a method 20 of detecting the *F. tularensis* species, a subspecies thereof, a subtype thereof, or a combination thereof is described in greater detail. The method 20 begins with obtaining a suspect specimen that the operator would desire a test for the presence of *F. tularensis* (or *F. tularensis* nucleic acid) or related bacteria (or bacterial nucleic acid) (Block 22). Such specimen may be, but is not limited to, food, water, soil, insects, arthropods, and human clinical specimens. Genomic DNA is extracted from the suspected specimen by standard methods or other practical means (Block 24). For PCR, however, and as would be understood by the skilled artisan, the specimen may be directly assessed using such methods without the need for isolation of genomic DNA (Optional Block 26).

Depending on the method employed (i.e., PCR, qPCR, sequencing) the next steps vary, as would be understood by one having ordinary skill in the art and the benefit of the disclosure provided herein (Decision Block 28).

For qPCR ("qPCR" branch of Decision Block 28) primers and probes are selected and prepared according to a desired level of detection, wherein the desired detection level may be species, subspecies, or subtype (Block 30). Alternatively, ("PCR SEQUENCE" branch of Decision Block 28), primers are selected and prepared according to a desired level of detection, wherein the desired detection level may be species, subspecies, or subtype (Block 30'). Generally, the composition and formula of the reaction is dependent on the make and model of the instruments to be employed, as well as whether the reaction is performed singleplex or multiplex. Likewise, probe fluorophores (and quenchers in qPCR variants) are selected for detection by the intended instrument. Such compositions, formulations, and preparations are known to those having ordinary skill in the art and the benefit of the disclosure provided herein.

The desired detection level may be determined by selecting at least one assay from a plurality of assays, each assay comprises sequences for a forward primer, a reverse primer, and a probe (for qPCR) that are specific to a subtype of, a subspecies of, or the *F. tularensis* species, or to general, related bacteria, broadly. Such sequences are provided in detail below, in Table 1. Specifically, the individual assays of Table 1, "U16S," "4Pan1," "3Pan," "A1d," "A2c," "B2," and "M3," produce a product corresponding to only with certain *F. tularensis* variants or related bacteria, generally. By observing products for the selected assays, by any preferred means of visualization, the strain of *F. tularensis* encountered may be determined.

The genomic signatures of Table 1 detect only the intended strains of interest, are compatible with the other primers and probes of Table 1, are compatible with other commercially-available primers and probes, and provide specific and sensitive identification of the strain or strains of interest. The primers and probes according to embodiments of the present invention anneal to complementary chromosomal regions in the *F. tularensis* strain or strains of interest described in greater detail below. The location in the genome of the primers was chosen to provide this desired result without the direct intervention of the operator.

Each assay yields information such that the encountered strain is determined by deduction. Therefore, each selection includes a negative control assay, a positive control assay, and at least one identifying assay. A product of the negative control assay sequence facilitates a determination of whether a contaminant is present (e.g., DNA template carry over); a product of the positive control assay sequence (i.e., an appropriate DNA target) suggests no inhibitors are present in the reaction and reagents are functioning as expected.

According to some embodiments of the present invention, the "U16S" assay, provided in Table 1, may be used as the positive control and reveals whether any bacterium is present within the specimen.

According to embodiments of the present invention, the negative control assay sequence may comprise a small, synthetic plasmid, tailored to pair with appropriate primers.

Optionally, the absence of inhibitors may be validated by spiking the reaction containing the specimen with the appropriate components, such as the U16S primers and amplicon, and omitting the probe for conventional PCR (or including the probe for qPCR). Such assay will yield a positive product for any sample containing bacterial DNA and provides evidence that the PCR or qPCR reaction was not inhibited. Determination of non-inhibition enables an operator to correctly assess a negative result. Without a proper amplification control, the operator may falsely assume that no product production means that *F. tularensis* is not present in the sample being tested, when in reality, the assay has failed to work due to the presence of inhibitory compounds or substances.

The modified, universal 16S ribosomal DNA (rDNA) assay of Table 1 is an endogenous internal control configured to amplify the conserved region in the 16S rRNA gene of the bacterial strains in the sample or, alternatively, for use as an exogenous reagent or assay control. The conventional, universal 16S rDNA probe sequence was slightly modified to accommodate the *Francisella* genus and *Francisella*-like organisms.

The 4Pan1 assay sequences, as shown in Table 1, detect all four *F. tularensis* subspecies, including avirulent subspecies *novicida*, in a PCR-based assay, a singleplex qPCR assay, a nonmatrix-based (or matrix-based) multiplex qPCR assay, or a sequencing-based assay. The targeted region in the 4Pan1 assay is highly conserved in all four *F. tularensis* subspecies and is located within the ostA1 gene (or the ostA2 gene) or nucleotide sequences with similarity to a region within the *F. tularensis* locus tag FTT_467. The 4Pan1 assay will only yield a product for a specimen having at least one *F. tularensis* variant, but not for any closely related bacteria.

The 3Pan assay sequences, as shown in Table 1, detect the three virulent *F. tularensis* subspecies and therefore, excludes avirulent subspecies *novicida* in a PCR-based assay, a singleplex qPCR assay, a nonmatrix-based (or matrix-based) multiplex qPCR assay, or a sequencing based-assay. The targeted region in the 3Pan assay is present and highly conserved in only the three virulent *F. tularensis* subspecies (*tularensis* subtype A.I and A.II, *holarctica*, and *mediasiatica*) and is located within nucleotide sequences that shares similarity to a region within the *F. tularensis* locus tag FTL_1858. The 3Pan assay will only yield a product for a specimen having at least one of the three virulent *F. tularensis* subspecies, i.e., *tularensis* (type A), *holarctica* (type B), and *mediasiatica*.

The A1d assay sequences, as shown in Table 1, detect only the *F. tularensis* subspecies *tularensis* subtype A.I strains in a PCR-based assay, a singleplex qPCR assay, a nonmatrix-based (or matrix-based) multiplex qPCR assay, or a sequencing-based assay. The targeted region in the A1d assay is present and highly conserved in only *F. tularensis* subspecies *tularensis* subtype A.I and is located within nucleotide sequences that shares similarity to a region within the *F. tularensis* locus tag FTT_0516. The spatial location where the primers and probe bind the chromosome of *F.*

*tularensis* subspecies *tularensis* subtype A.I strains provides the specificity. The A1d assay will only yield a product for a specimen having the *F. tularensis* subspecies *tularensis* subtype A.I, which is the most serious threat and the most virulent clad of the *F. tularensis* species, as well as most other bacterial pathogens.

The A2c assay sequences, as shown in Table 1, detect only *F. tularensis* subspecies *tularensis* subtype A.II strains in a PCR-based assay, a singleplex qPCR assay, a nonmatrix-based (or matrix-based) multiplex qPCR assay, or a sequencing-based assay. The targeted region of the A2c assay is present and highly conserved in only the *F. tularensis* subspecies *tularensis* subtype A.II strains and is located within the gene mviN, which is predicted to encode an integral membrane protein. The nucleotide sequences shares similarity to a region within the *F. tularensis* locus tag FTW_1702. The A2c assay will only yield a product for a specimen having the moderately virulent *F. tularensis* subspecies *tularensis* subtype A.II.

The B2 assay sequences, as shown in Table 1, detect only *F. tularensis* subspecies *holarctica* (type B) strains in a PCR-based assay, a singleplex qPCR assay, a nonmatrix-based (or matrix-based) multiplex qPCR assay, or a sequencing-based assay. The targeted region in the B2 assay is present and highly conserved in only the *F. tularensis* subspecies *holarctica* (type B) strains and is located within nucleotide sequences that shares similarity to a region within the *F. tularensis* locus tag FTS_0806. The B2 assay will only yield a product for a specimen having the moderately virulent *F. tularensis* subspecies *holarctica* (type B).

The M3 assay sequences, as shown in Table 1, detect only *F. tularensis* subspecies *mediasiatica* strains in a PCR-based assay, a singleplex qPCR assay, a nonmatrix-based (or matrix-based) multiplex qPCR assay, or a sequencing-based assay. The targeted region in the M3 assay is present and highly conserved in only the *F. tularensis* subspecies *mediasiatica* strains and is located within nucleotides sequences that shares similarity to a region within the *F. tularensis* locus tag FTM_1104. The spatial location where the primers bind the chromosome of *F. tularensis* subspecies *mediasiatica* strains provides the specificity. The M3 assay will only yield a product for a specimen having the moderately virulent *F. tularensis* subspecies *mediasiatica*.

The N1, N2, N3, and N4 assays will only yield a product for a specimen having the non-virulent *F. tularensis* subspecies *novicida*. The N1 assay sequences, as shown in Table 1, detect only *F. tularensis* subspecies *novicida* strains in a PCR-based assay, a singleplex qPCR assay, a nonmatrix-based (or matrix-based) multiplex qPCR assay, or a sequencing-based assay. The targeted region of the N1 assay is present and highly conserved in only the *F. tularensis* subspecies *novicida* strains and is located within nucleotide sequences that shares similarity to a region within the *F. tularensis* locus tag FTN_0003, a genetic locus predicted to encode a metabolite:H+ symporter protein.

The N2 assay sequences, as shown in Table 1, detect only *F. tularensis* subspecies *novicida* strains in a PCR-based assay, a singleplex qPCR assay, a nonmatrix-based (or matrix-based) multiplex qPCR assay, or a sequencing-based assay. The targeted region in the N2 assay is present and highly conserved in only the *F. tularensis* subspecies *novicida* strains and is located within nucleotide sequences that shares similarity to a region within the *F. tularensis* locus tag FTN_0003, a genetic locus predicted to encode a metabolite:H+ symporter protein.

The N3 assay sequences, as shown in Table 1, detect only *F. tularensis* subspecies *novicida* strains in a PCR-based assay, a singleplex qPCR assay, a nonmatrix-based (or matrix-based) multiplex qPCR assay, or a sequencing-based assay. The targeted region in the N3 assay is present and highly conserved in only the *F. tularensis* subspecies *novicida* strains and is located within nucleotide sequences that shares similarity to a region within the *F. tularensis* locus tag FTN_1015, a genetic locus predicted to encode an isochorismatase family protein.

The N4 assay sequences, as shown in Table 1, detect only *F. tularensis* subspecies *novicida* strains in a PCR-based assay, a singleplex qPCR assay, a nonmatrix-based (or matrix-based) multiplex qPCR assay, or a sequencing-based assay. The targeted region in the N4 assay is present and highly conserved in only the *F. tularensis* subspecies *novicida* strains and is located within nucleotide sequences that shares similarity to a region within the *F. tularensis* locus tag FTN_0730, a genetic locus predicted to encode an acyl-coenzyme A synthetase/AMP (fatty) acid ligase protein.

Collectively the primers, with or without the associated probes of the assays may, be employed to amplify a product ranging from 80 bp to 206 bp.

Figure 3:
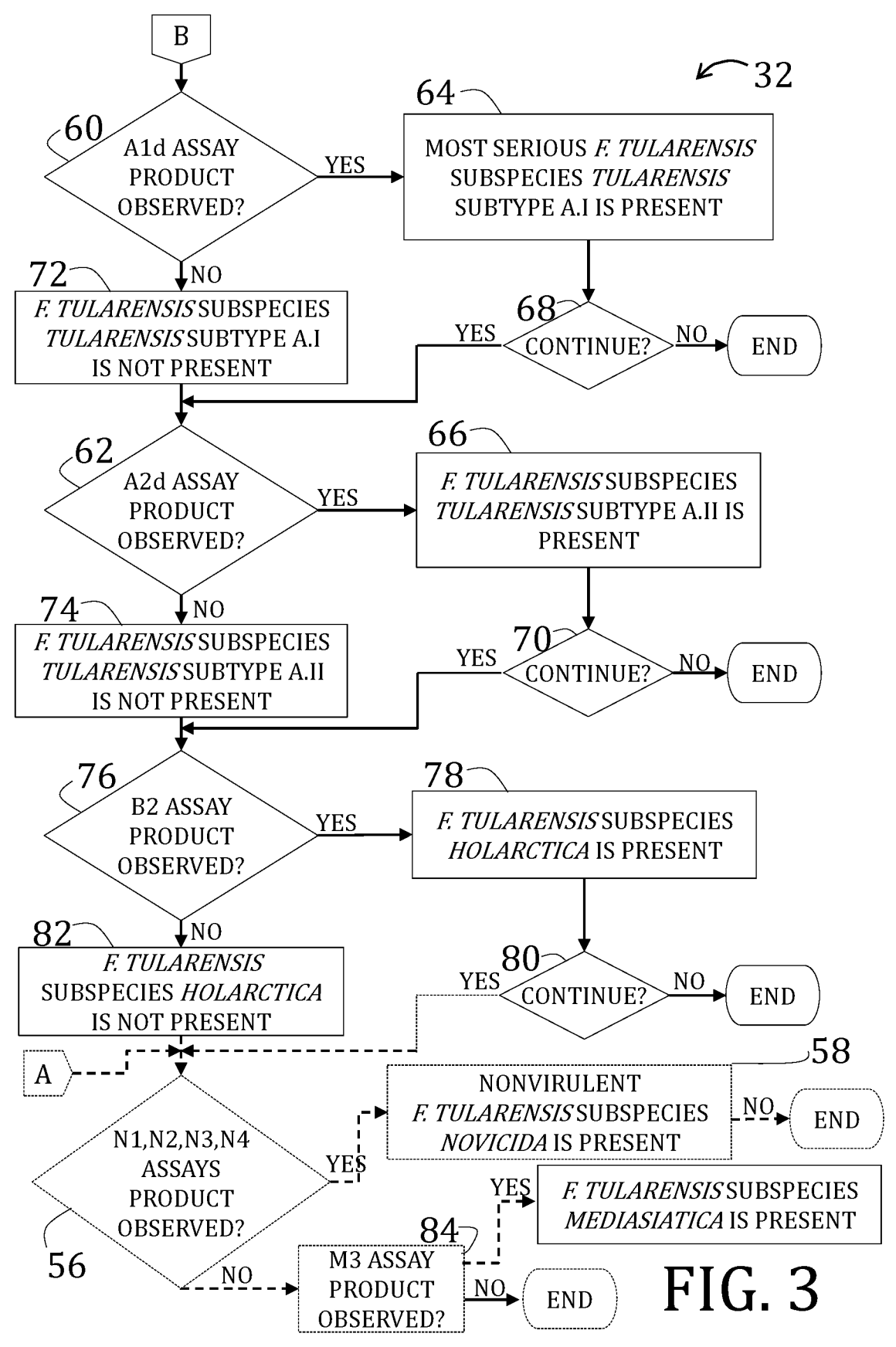

FIGS. 2 and 3 include a flowchart 32 illustrating a method of analyzing results from the assays denoted in Table 1 according to an embodiment of the present invention. The flowchart 32 may be used in determining which assays are selected. At start, a determination as to whether contamination is present within the specimen is made (Decision Block 34), which may also be considered to be a quality control check of the sample preparation. If a product results ("YES" Branch of Decision Block 34), then a contaminant may be present and the sample preparation fails quality control (Block 36). If no ("NO" Branch of Decision Block 34), then a determination as to whether a bacterium is present within the specimen is made (Decision Block 38). If no product is observed ("NO" Branch of Decision Block 38), then either no bacteria is present or the reaction failed due to a presence of inhibitors (for example) (Block 40). Confirmation of reaction failure may optionally be performed by diluting the sample and returning to Decision Block 34 (not shown); otherwise, the process ends. If a product is observed ("YES" Branch of Decision Block 38), the presence of bacteria (or bacterial nucleic acid) is confirmed and the process continues (Block 42).

Continuing, the 4Pan1 assay (Decision Block 44) provides a determination as to whether the bacterium present within the specimen is *F. tularensis*. If a product results ("YES" Branch of Decision Block 44), then *F. tularensis* is present (Block 46); otherwise ("NO" Branch of Decision Block 44), the bacterium present in the specimen is not *F. tularensis* and the process ends (Block 48). With a determination that *F. tularensis* is present within the sample, the assay may be used to further determine the subspecies and subtype (if appropriate) of the *F. tularensis* within the specimen.

The 3Pan1 assay (Decision Block 50) may be used to determine whether the *F. tularensis* subspecies present in the sample is one of the three virulent subspecies. If the assay yields a product ("YES" Branch of Decision Block 50), then at least one of the three virulent subspecies is present (Block 52). If the assay does not yield a product ("NO" Branch of Decision Block 50), then the *F. tularensis* that is present within the sample may be the *novicida* subspecies (Block 54); however, such determination is not definitive. For confirmation of the presence of the subspecies *novicida* (or subsp. *novicida* nucleic acid), the method may optionally continue (Optional Arrow A) to further determination by one or more of the N1, N2, N3, and N4 assays (Decision Block

56, FIG. 3). If a product results from one or more of these assays ("YES" Branch of Decision Block 56), then the nonvirulent *F. tularensis* subspecies *novicida* is present (Block 58).

Returning again to FIG. 2, and continuing from the observation that at least one virulent strain of *F. tularensis* is present within the specimen (Block 52), the method continues (Arrow B) into FIG. 3 to determine whether the subspecies of *F. tularensis* is subsp. *tularensis* and, if so, which subtype.

The A1d and A2d assays (Decision Blocks 60 and 62, respectively) enable a determination as to whether the *F. tularensis* within the specimen is subspecies *tularensis* subtype A.I or subspecies *tularensis* subtype A.II, respectively. If either assay yields a product ("YES" Branches of Decision Blocks 60 and 62), then the respective subtype is present within the specimen (Blocks 64 and 66). If further determination is desired ("YES" Branches of Decision Blocks 68 and 70), the methods may continue; otherwise ("NO" Branches of Decision Blocks 68 and 70), the methods end. Yet, if no assay product is observed ("NO" Branches of Decision Blocks 60 and 62), the respective subtype is not present (Blocks 72 and 74) and the process may continue.

A determination of whether the specimen contains the subspecies *holarctica* is made using the B2 assay (Decision Block 76). If the reaction yields a product ("YES" Branch of Decision Block 76), then the subspecies *holarctica* is present (Block 78) and a decision is made as to whether further analysis is desired (Decision Block 80); if no product ("NO" Branch of Decision Block 76), then the subspecies *holarctica* is not present (Block 82). If desired, the N1, N2, N3, and N4 assay (Decision Block 56) may be used to determine whether the *novicida* subspecies is present. If no product is observed ("NO" Branch of Decision Block 56), then the M3 assay may be used to determine whether the *mediasiatica* subspecies is present (Block 84).

Figure 4:
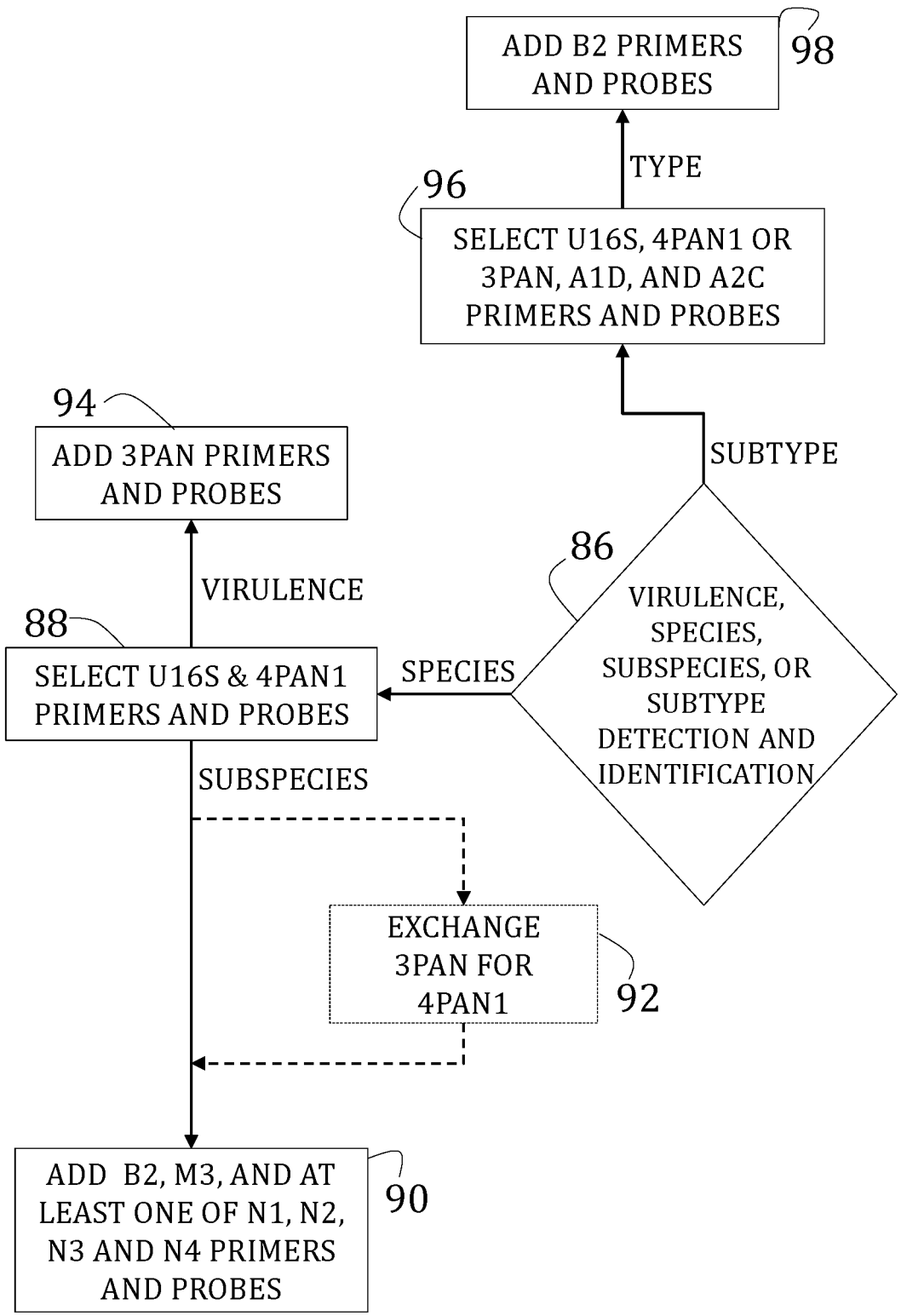

It would be understood by those having ordinary skill in the art that not all assays provided in Table 1 are necessary for every determination. Instead, as shown in FIG. 4, the number and type of assays selected depends on the desired detection level. For example, if the desired detection level is to assess whether the *F. tularensis* species is present ("SPECIES" Branch of Decision Block 86), then only the U16S and 4PAN1 assays are necessary (Block 88). If further determination of subspecies is desired ("SUBSPECIES" Branch from "SPECIES" Branch of Decision Block 86), then the B2, M3, and at least one of N1, N2, N3, and N4 assay need be used (Block 90). Optionally, in determining subspecies, the 3PAN assay may be used in addition to in or place of the 4PAN1 assay (Block 92). Alternatively, if the virulence of the detected species or subspecies is desired ("VIRULENCE" Branch from "SPECIES" Branch of Decision Block 86), then the 3PAN assays are necessary (Block 94). If subtype is desired, ("SUBTYPE" Branch of Decision Block 86), then U16S, 4PAN1 (alternatively or also including 3PAN), A1D, and A2C assays are necessary (Block 96). If type is desired ("TYPE" Branch from "SUBTYPE" Branch of Decision Block 86), then the B2 primers and probes are also necessary (Block 98).

Referring again to FIG. 1, and with the desired detection level and appropriate primers/probes selected (Blocks 30 and 30') and prepared, an appropriate reaction may be prepared. As to PCR and qPCR, a high stringency conventional PCR reaction may proceed (Blocks 100, 102). As to sequencing, a low stringency PCR may be used (Block 104). The low stringency PCR reaction generates background amplification and permits some miss-priming, which extends the number of products generated by the detectors. The prepare reactions may be executed according to the particular parameters for the equipment and instruments used and as would be understood by the skilled artisan (Block 106) and products of the reactions observed (Block 108). PCR only variants may be scored via intercalating dyes (e.g., SYBR Green) or by directly observing the amplified and stained DNA following gel fractionation, if desired. Amplification using qPCR is diagnostic for the various strain types and hydrolysis of the probe provides a quantitative measurement of the detected genomic DNA that is observed by real-time fluorescence.

Analysis of the results may be performed according to any one of several different methods (Block 110) and the concentration of amplified DNA may be determined using standard molecular biology methods. The resulting DNA products may then be pooled and sequenced in accordance with the methods and instructions of any given manufacture of sequencer instrumentation. The resulting DNA data may be assembled into theoretical contiguous DNA pieces using any assembler software suited to the task. The assembly corrects errors and removes duplicated data, making the analysis easier.

Figures 6A, 6B:
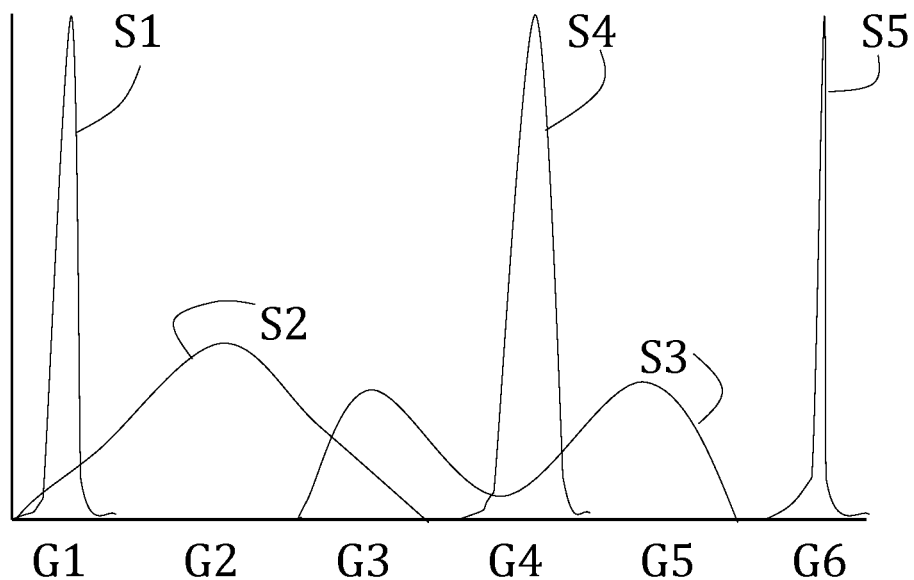
FIGS. 6A and 6B illustrate a method of analyzing data from sequencing embodiments of the present invention.

Turning now to FIGS. 5, 6A, and 6B, methods of analyzing data from sequencing embodiments of the present invention, Sequencing Reactions (Block 104, FIG. 1), are described. The result of the low stringency PCR techniques may be a complex amplicon library, which may be larger than PCR or RT-PCR variants. Such resultant amplicon library may comprise diagnostic sequences associated with *F. tularensis* or other, less predictable sequences derived from the genome of other known and/or unknown bacterium within the specimen. Altogether, the amplicon library provides a highly unique fingerprint for each *F. tularensis*. Collectively the sequencing variant sequences between 600 bases and 3000 bases of DNA from each *F. tularensis* subspecies.

For some embodiments of the present invention, the amplicon library may be analyzed according to methods described in U.S. Provisional Application No. 62/474,604, and U.S. application Ser. No. 15/908,765, both entitled METHOD FOR DETECTION AND STRAIN IDENTIFICATION OF KNOWN AND EMERGENT PATHOGENS, by James Baldwin, filed on Feb. 28, 2017 and Feb. 28, 2018, respectively, the details of said application being incorporated herein by reference, in its entirety. One exemplary method 112 is illustrated in FIG. 5A, whereby resultant sequences of the amplicon library may be subjected to in silico filtration and processing. Such filtration may be accomplished using any computing device commonly utilized for such tasks. According to some preferred embodiments of the present invention, the computing device will sequence products in a highly parallel and cost-effective manner. Thus, the computing system may make use of any conventional computer-networking to connect the computing system to at least one server hosting suitable software. Cloud computing is optional in some embodiments.

At start, sequences of the amplicon library may be optionally filtered (Block 114) so as to remove undesired sequences. Such undesired sequences may include, for example, human DNA or human RNA if the specimen was human in nature. Of the remaining sequences within the filtered amplicon library, a number (n) are randomly selected to form a set (Block 116). While n may vary, and depends largely on the number of sequences within the amplicon library, an n value of 100 may be considered typical.

The sequences of the set may be compared to known sequences associated with *F. tularensis* (Block 118). Additionally, or alternatively, although not specifically illustrated herein, the sequences of the set may be searched against an appropriate database, such as a derivative of GenBank using the National Center for Biotechnology Information ("NCBI") Basic Alignment Search Tool ("BLAST") or the Bowtie 2 (Johns Hopkins University, Baltimore, MD) algorithms. The GenBank database contains the completed or partially sequenced genomes for identified *F. tularensis* strains and related bacteria, including the completed or partially sequenced 16S ribosomal genes for identified bacteria of interest.

If a sequence within the set maps to an *F. Tularensis* sequence (or to a larger database if implemented) ("YES" branch of Decision Block 120), then the sequence from the set and an identity of the mapped sequence are logged as "matched" (Block 122). Otherwise, ("NO" branch of Decision Block 124), the sequence from the set is logged as "unmatched" (Block 124).

With all sequences of the set mapped and logged (Blocks 122, 124), a decision is made as to whether continuation is necessary (Decision Block 126). If continuation is desired, ("YES" branch of Decision Block 126), the method returns such that n samples are again randomly sampled from the amplicon library to form the set (Block 116). If no continuation is needed ("NO" branch of Decision Block 126), for instance, a previous set of sequences did not yield novel result—a new *F. tularensis* sequence match, a new database match, or a new unmapped sequence—then the process may end.

Facultative identification determined according to the method 112 of FIG. 5, wherein each sequence of the set may be correlated with known genomes as shown in FIG. 6A. In some instances, which may be probable for sequences associated with the A1d, A2c, B2, and M3 (for example, S1, S4, and S5 of FIG. 6A) the result may be a single hit. Thus, accurate strain identification may be determined if an exact sequence match occurs to an organism in the database or listing of *F. tularensis* sequences.

Alternatively, the result may be part of a detection group (an exact or complete sequence match), which is probable for U16S (for example, S2 and S3 of FIG. 6A, wherein an asterisk indicates a group match). For example, a given U16S amplicon product may be a near exact match to many related strains because each strain will possess some homology. As such, the product is not specifically diagnostic, but does identify the presence of bacteria or bacterial nucleic acids. Therefore, the full list of all potential detections in a facultative identification may be reported. Moreover, the U16S assay may provide a DNA barcoding assay of sorts. The enclosed control-barcoding detector, when used with the more specific *F. tularensis* assays described in accordance with embodiments of the present invention, provides cooperative identification and exclusion effects via multilocus sequencing for every strain in the sample.

After an entropy score (the number of unique *Francisella* strains that share this sequence tag) is determined for each sequence in the set, that mapping may be equal to the number of genome/strain matches for that respective sequence. In the illustrated example of FIG. 6A, Si is provided as an entropy value of 1, S2 is provided as an entropy value of 3, and so forth. For instance, if the entropy score is one, then only one genome/strain is identified and the identity of that genome/strain may be recorded as the closest identification.

If multiple genomes (or detection groups) are matched by the detected DNA products (as in S2 and S3), then such results may be combined to form a detection group (FIG. 6B). The exact composition of each group may vary due to other sequences in the genome. Should only one strain exist, this "smallest common strain list" can provide the exact identification.

TABLE 1

| SEQ. NO. | DETECTOR ASSAY | TYPE | SEQUENCE | LENGTH | STRAINS DETECTED |
|---|---|---|---|---|---|
| 1 | U16S | Forward Primer | 5'-TGGAGCATGTGGTTTAATTCGA | 22-mer | Endogenous internal control |
| 2 | | Reverse Primer | 5'-TGCGGGACTTAACCCAACA | 19-mer | |
| 3 | | Probe | 5'-F-CACGAGCTGACGACARCCRTGCA-Q | 23-mer | |
| 4 | 4Pan1 | Forward Primer | 5'-CAYCCTAGACTATTCTATACTTAC | 24-mer | All four subspecies |
| 5 | | Reverse Primer | 5'-GTAAATCTATTTACTTGAAACATCTGC | 27-mer | |
| 6 | | Probe | 5'-F-CCGTACCAAGATCAAACAAATATACC-Q | 26-mer | |
| 7 | 3Pan | Forward Primer | 5'-TTTACACCCGTCTCCGTTAGT | 21-mer | Three virulent subspecies |
| 8 | | Reverse Primer | 5'-CTCTTAAGGATGCAATTTGGGATT | 24-mer | |
| 9 | | Probe | 5'-F-AAGAGGCAAAGCTGGAATTACACTCTCTC-Q | 29-mer | |
| 10 | A1d | Forward Primer | 5'-CACCCAGCAACAAAGTAGCAC | 21-mer | Only *tularensis* subtype A.I |
| 11 | | Reverse Primer | 5'-CTATCTCATCATCAAAATCTATAAGAGC | 28-mer | |
| 12 | | Probe | 5'-F-CTCTTGCTGTTTTTTTAGCTGGATTATCC-Q | 29-mer | |
| 13 | A2c | Forward Primer | 5'-GGCTTTGCTAGCACAAATAAACC | 23-mer | Only *tularensis* subtype A.II |
| 14 | | Reverse Primer | 5'-GATAAACAGCAATTCTTTAAGACGAC | 26-mer | |
| 15 | | Probe | 5'-F-CACTGTTAGTGACAATCCCTGCTATAG-Q | 27-mer | |

TABLE 1-continued

| SEQ. NO. | DETECTOR ASSAY | TYPE | SEQUENCE | LENGTH | STRAINS DETECTED |
|---|---|---|---|---|---|
| 16 | B2 | Forward Primer | 5'-CCTATCCAATACTCCGAGTTAGT | 23-mer | Only *holarctica* (type B) |
| 17 | | Reverse Primer | 5'-AAATCAAAAGAAGAGTTAAAACAAGC | 26-mer | |
| 18 | | Probe | 5'-F-CTCTGGCCAGTTATTTTTATCAAAGCCAG-Q | 29-mer | |
| 19 | M3 | Forward Primer | 5'-AGCACATGCTAGTTTAATGAGTT | 23-mer | Only *mediasiatica* |
| 20 | | Reverse Primer | 5'-ACTAGTTGATGCAGAGTTACC | 21-mer | |
| 21 | | Probe | 5'-F-CTACACCCATTTGGGAAATGCCTTC-Q | 25-mer | |
| 22 | N1 | Forward Primer | 5'-CTTGTTGTGGTAAAAATAGCTTAG | 24-mer | Only *novicida* |
| 23 | | Reverse Primer | 5'-GGAAGTTTTCATGAGTAAGAGC | 22-mer | |
| 24 | | Probe | 5'-F-CAATAACTGGCGCAGCAAACATACCATAC-Q | 29-mer | |
| 25 | N2 | Forward Primer | 5'-CTTTCTAAAATAAATGCAGCTGCT | 24-mer | Only *novicida* |
| 26 | | Reverse Primer | 5'-TCCTATATTTCTGATGCTTATCAG | 24-mer | |
| 27 | | Probe | 5'-F-CCACCAATTTCYCCACCAACAGCAAATC-Q | 28-mer | |
| 28 | N3 | Forward Primer | 5'-GATCAGCTCCTATAACCATTTTC | 23-mer | Only *novicida* |
| 29 | | Reverse Primer | 5'-GCTT-AAAGAGCTACTACAAAAAA-TC | 25-mer | |
| 30 | | Probe | 5'-F-AAGGAACAATTCCATCATCAAACAT-ATCC-Q | 29-mer | |
| 31 | N4 | Forward Primer | 5'-GCAAAAGAATAGCTATGAAAGC | 22-mer | Only *novicida* |
| 32 | | Reverse Primer | 5'-CTCTTGGGTATAGCAGATATC | 21-mer | |
| 33 | | Probe | 5'-F-AATTTCAGCAACAACCTTATCAACAGC-Q | 27-mer | | wherein R = A or G and Y = T or C.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1

Limit of detection ("LOD") ranges were dependent on fluorophores and quenchers utilized in the probe and the qPCR instrument used.

The LOD for the *F. tularensis* species-, subspecies-, and subtype-specific singleplex qPCR assays ranged from 1 fg to 5 fg of *F. tularensis* genomic DNA on the JBAIDS or LIGHTCYCLER (F. Hoffman-La Roche AG, Basel, Switzerland), as illustrated in FIGS. 7, 8, 9, 10, 11, 12, and 13. The graphically illustrated data of these figures are provided in Tables 2-8, respectively, below.

Ten-fold dilutions of *F. tularensis* genomic DNA of certain tests resulted in a linear standard curve for all of the *F. tularensis* species-, subspecies, and subtype-specific singleplex qPCR assays, which are specifically illustrated in FIGS. 12A, 14A, 15A, 16A, 17A, 18A, and 19A.

Figure 7:
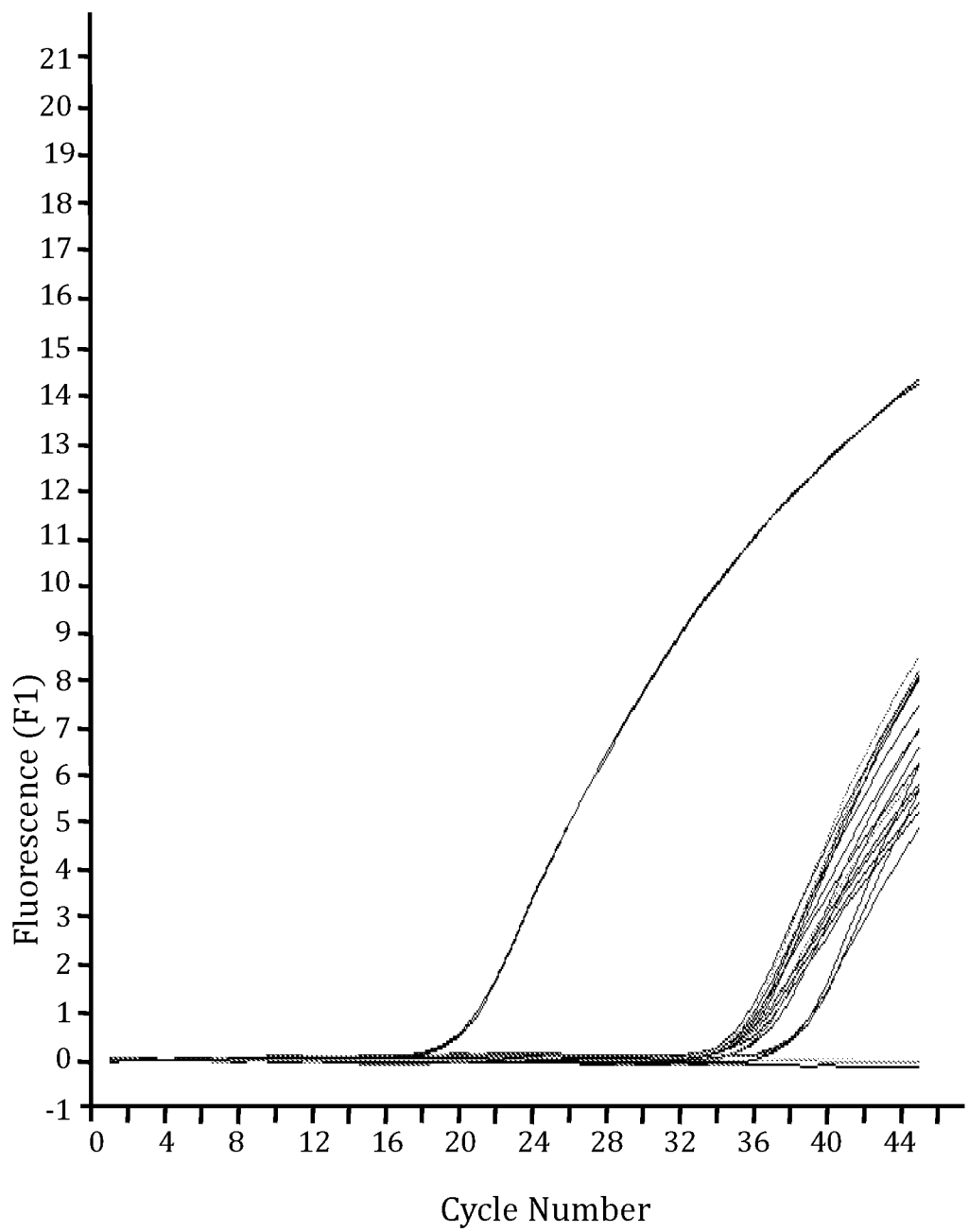
FIGS. 7-19 graphically illustrate detection of *F. tularensis* species, subspecies-, and subtypes using a singleplex assay.

As illustrated in FIG. 7 and provided in Table 2, below, the 4Pan1 real-time qPCR assay according to embodiments of the present invention detects all four *F. tularensis* subspecies, including avirulent subspecies *novicida*. The limit of detection for the 4Pan1 real-time qPCR assay was determined to be less than 3 fg and greater than 1 fg.

Optimized conditions for 16S assay (5 mM $MgCl_2$, 0.5 µM Forward primer, 0.5 µM Reverse primer, and 0.2 µM TaqMan probe), 20 µL total reaction volume: 7.4 µL sterile water, 2 µL 10×PCR Buffer, 2 µL $MgCl_2$ [50 mM], 2 µL 10×dNTP mix, 2 µL 16S Forward primer [10 µM], 1.5 µL 16S Reverse primer [10 µM], 1.5 µL 16S-P probe [4 µM], 0.5 µL BSA [10 mg/mL], 0.1 µL Platinum Taq [5 U/µL], and 1 µL DNA template.

TABLE 2

4PAN1 REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control | Positive | 20.16 | 14.4 |
| Positive Control | Positive | 20.18 | 14.4 |
| LVS (10 fg) | Positive | 34.82 | 8.2 |
| LVS (10 fg) | Positive | 35.38 | 8.1 |
| LVS (10 fg) | Positive | 38.24 | 6.2 |
| LVS (10 fg) | Positive | 35.49 | 8.3 |
| LVS (7 fg) | Positive | 35.14 | 8.5 |
| LVS (7 fg) | Positive | 35.70 | 8.0 |
| LVS (7 fg) | Positive | 36.18 | 7.0 |
| LVS (7 fg) | Positive | 36.51 | 6.6 |
| LVS (5 fg) | Positive | 35.02 | 7.5 |
| LVS (5 fg) | Positive | 35.14 | 7.0 |
| LVS (5 fg) | Positive | 35.33 | 6.2 |
| LVS (5 fg) | Positive | 34.89 | 6.4 |
| LVS (3 fg) | Positive | 35.76 | 5.2 |
| LVS (3 fg) | Positive | 35.47 | 5.4 |
| LVS (3 fg) | Positive | 35.39 | 5.7 |
| LVS (3 fg) | Positive | 35.48 | 5.9 |

TABLE 2-continued

4PAN1 REAL-TIME QPCR ASSAY

| SAMPLE | TARGET | CT VALUE | MAX FLUOR |
|---|---|---|---|
| LVS (1 fg) | Negative | — | — |
| LVS (1 fg) | Positive | 37.97 | 4.9 |
| LVS (1 fg) | Negative | — | — |
| LVS (1 fg) | Positive | 38.66 | 5.7 |

Figure 8:
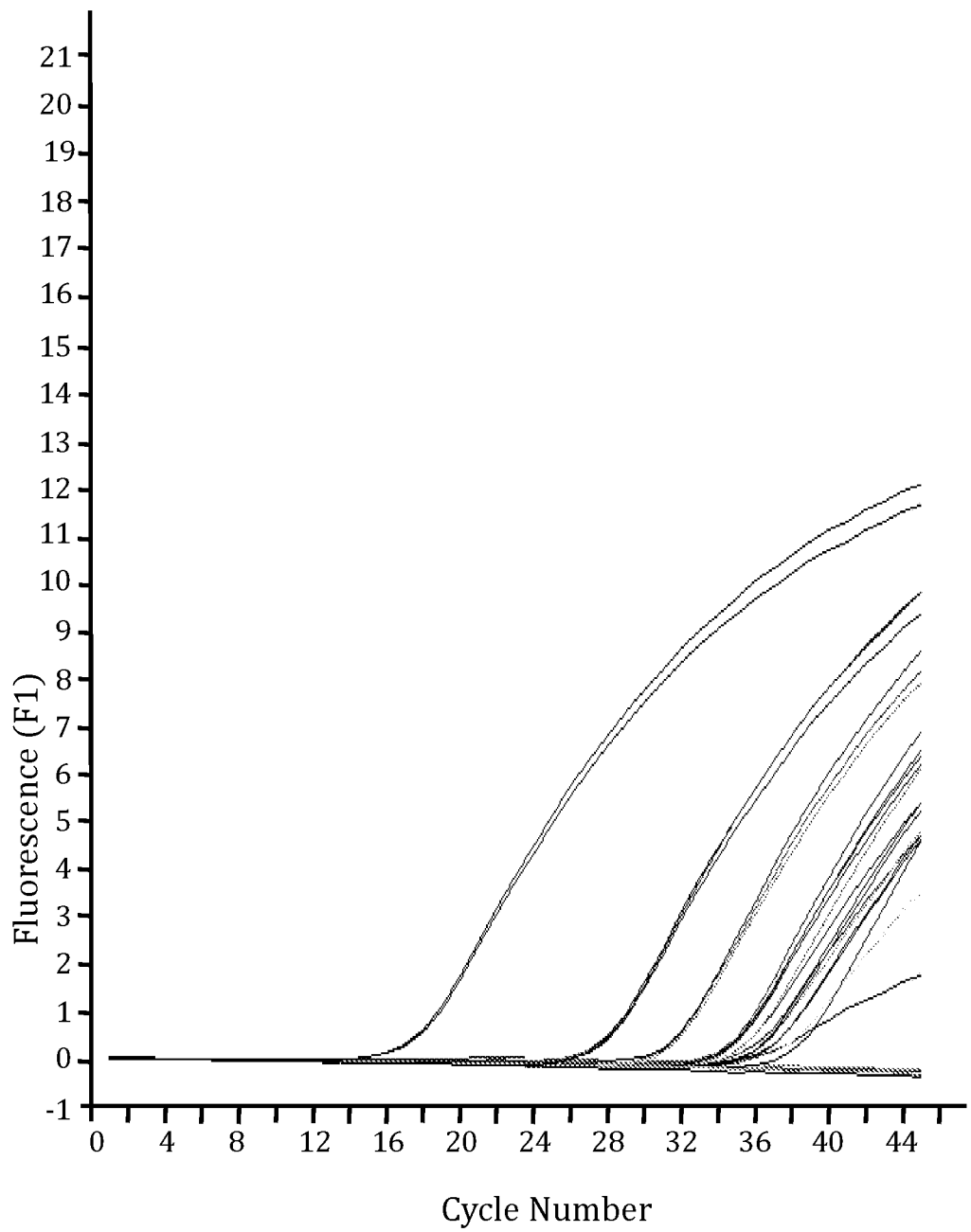

As illustrated in FIG. 8 and provided in Table 3, below, the 3Pan real-time qPCR assay was developed to detect all three of the virulent *F. tularensis* subspecies and not the avirulent subspecies *novicida*. The limit of detection for the 3Pan real-time qPCR assay was determined to be less than 1 fg and greater than 0.1 fg, which is 1 genome equivalent.

Optimized conditions for 4Pan1 assay (5 mM MgCl$_2$, 0.5 µM Forward primer, 0.75 µM Reverse primer, and 0.3 µM TaqMan probe), 20 µL total reaction volume: 8.4 µL sterile water, 2 µL 10×PCR Buffer, 2 µL MgCl$_2$ [50 mM], 2 µL 10×dNTP mix, 1 µL 4Pan1 Forward primer [10 µM], 1.5 µL 4Pan1 Reverse primer [10 µM], 1.5 µL 4Pan1-P probe [4 µM], 0.5 µL BSA [10 mg/mL], 0.1 µL Platinum Taq [5 U/µL], and 1 µL DNA template.

TABLE 3

3PAN REAL-TIME QPCR ASSAY

| SAMPLE | TARGET | CT VALUE |
|---|---|---|
| Negative Control | Negative | — |
| Negative Control | Negative | — |
| Positive Control | Positive | 17.69 |
| Positive Control | Positive | 17.67 |
| LVS (1000 fg) | Positive | 27.91 |
| LVS (1000 fg) | Positive | 27.80 |
| LVS (1000 fg) | Positive | 27.81 |
| LVS (100 fg) | Positive | 31.44 |
| LVS (100 fg) | Positive | 31.54 |
| LVS (100 fg) | Positive | 31.66 |
| LVS (10 fg) | Positive | 34.67 |
| LVS (10 fg) | Positive | 34.65 |
| LVS (10 fg) | Positive | 38.24 |
| LVS (7 fg) | Positive | 34.72 |
| LVS (7 fg) | Positive | 35.43 |
| LVS (7 fg) | Positive | 34.73 |
| LVS (5 fg) | Positive | 36.01 |
| LVS (5 fg) | Positive | 36.25 |
| LVS (5 fg) | Positive | 35.22 |
| LVS (3 fg) | Positive | 36.81 |
| LVS (3 fg) | Positive | 36.17 |
| LVS (3 fg) | Positive | 35.82 |
| LVS (1 fg) | Positive | 37.34 |
| LVS (1 fg) | Positive | 36.13 |
| LVS (1 fg) | Positive | 36.81 |
| LVS (0.1 fg) | Negative | — |
| LVS (0.1 fg) | Negative | — |
| LVS (0.1 fg) | Negative | — |

Figure 9:
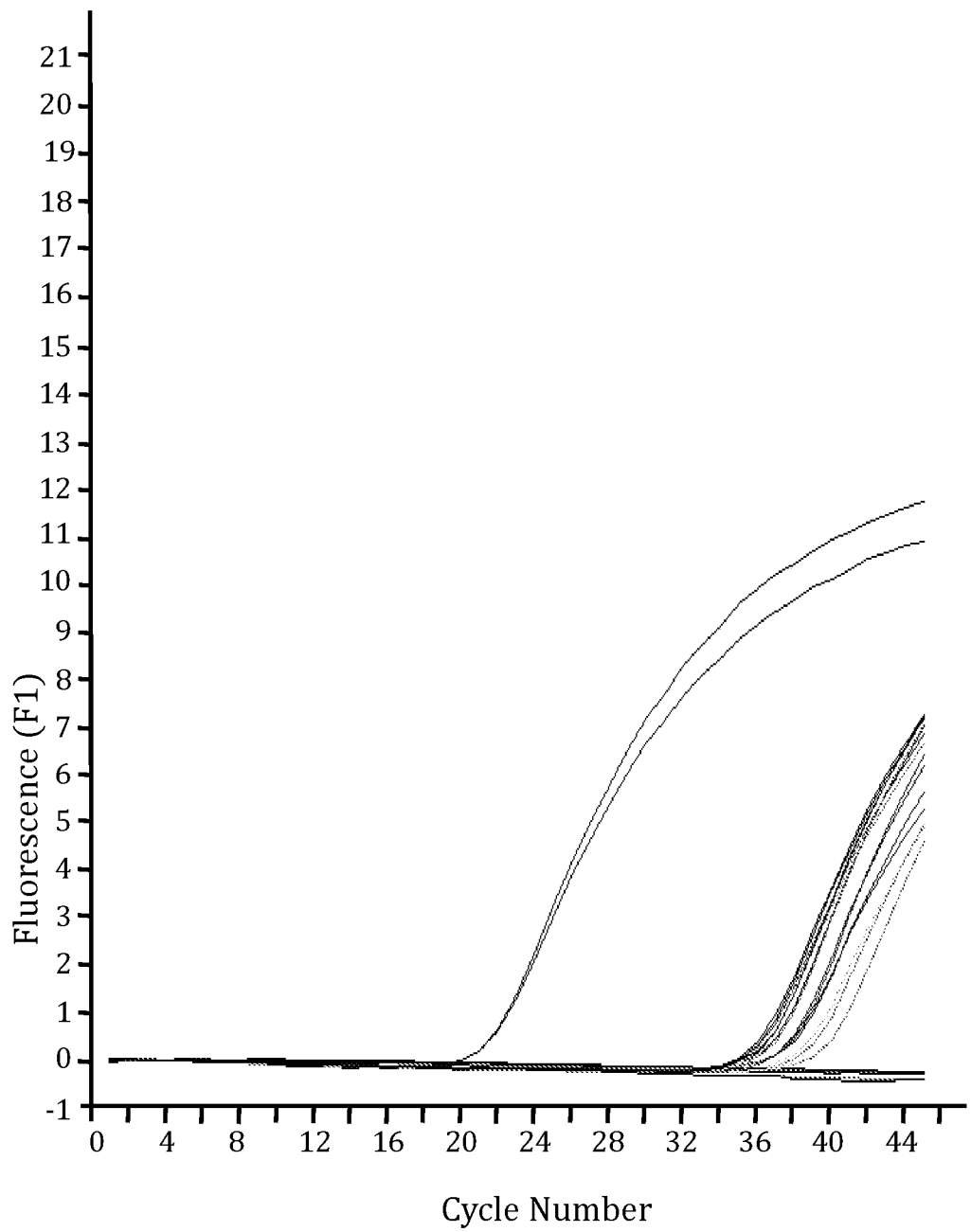

As illustrated in FIG. 9 and provided in Table 4, below, the A1d real-time qPCR assay was developed to detect the highly virulent *F. tularensis* subspecies *tularensis* subtype A.I strains. The limit of detection for the A1d real-time qPCR assay was determined to be less than 7 fg and greater than 5 fg of *F. tularensis* subspecies *tularensis* subtype A.I genomic DNA.

Optimized conditions for 3Pan assay (5 mM MgCl$_2$, 0.5 µM Forward primer, 0.5 µM Reverse primer, and 0.4 µM TaqMan probe), 20 µL total reaction volume: 8.4 µL sterile water, 2 µL 10×PCR Buffer, 2 µL MgCl$_2$ [50 mM], 2 µL 10×dNTP mix, 1 µL 3Pan Forward primer [10 µM], 1 µL 3Pan Reverse primer [10 µM], 2 µL 3Pan-P probe [4 µM], 0.5 µL BSA [10 mg/mL], 0.1 µL Platinum Taq [5 U/µL], and 1 µL DNA template.

TABLE 4

A1D REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control | Positive | 21.64 | 11.8 |
| Positive Control | Positive | 21.35 | 11.0 |
| A1-1 (10 fg) | Positive | 37.15 | 6.3 |
| A1-1 (10 fg) | Positive | 35.78 | 7.3 |
| A1-1 (10 fg) | Positive | 35.81 | 7.2 |
| A1-1 (10 fg) | Positive | 36.68 | 7.1 |
| A1-1 (7 fg) | Positive | 38.86 | 4.6 |
| A1-1 (7 fg) | Positive | 36.12 | 7.3 |
| A1-1 (7 fg) | Positive | 37.48 | 6.5 |
| A1-1 (7 fg) | Positive | 36.53 | 7.0 |
| A1-1 (5 fg) | Positive | 36.24 | 7.3 |
| A1-1 (5 fg) | Positive | 35.90 | 6.8 |
| A1-1 (5 fg) | Positive | 35.92 | 6.7 |
| A1-1 (5 fg) | Negative | — | — |
| A1-1 (3 fg) | Negative | — | — |
| A1-1 (3 fg) | Positive | 37.59 | 5.7 |
| A1-1 (3 fg) | Negative | — | — |
| A1-1 (3 fg) | Positive | 37.25 | 5.3 |
| A1-1 (1 fg) | Positive | 38.78 | 5.0 |
| A1-1 (1 fg) | Negative | — | — |
| A1-1 (1 fg) | Positive | 38.21 | 4.9 |
| A1-1 (1 fg) | Negative | — | — |

Figure 10:
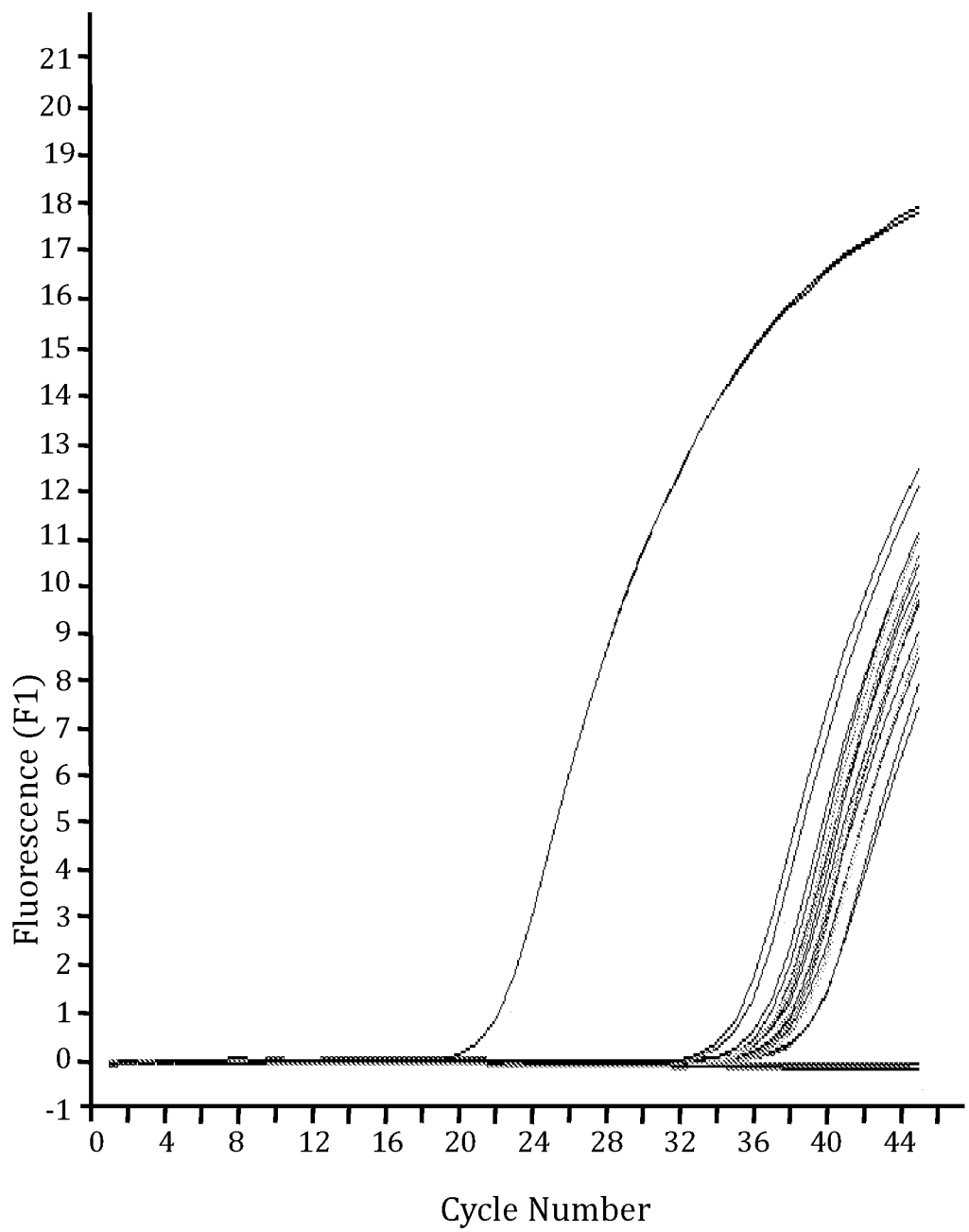

As illustrated in FIG. 10 and provided in Table 5, below, the A2c real-time qPCR assay was developed to detect *F. tularensis* subspecies *tularensis* subtype A.II strains. The limit of detection for the A2c real-time qPCR assay was determined to be less than 5 fg and greater than 3 fg of *F. tularensis* subspecies *tularensis* subtype A.II genomic DNA.

Optimized conditions for A1d assay (5 mM MgCl$_2$, 0.5 µM Forward primer, 0.5 µM Reverse primer, and 0.2 µM TaqMan probe), 20 µL total reaction volume: 9.4 µL sterile water, 2 µL 10×PCR Buffer, 2 µL MgCl$_2$ [50 mM], 2 µL 10×dNTP mix, 1 µL A1d Forward primer [10 µM], 1 µL A1d Reverse primer [10 µM], 1 µL A1d-P probe [4 µM], 0.5 µL BSA [10 mg/mL], 0.1 µL Platinum Taq [5 U/µL], and 1 µL DNA template.

TABLE 5

A2C REAL-TIM QPCR ASSAY

| SAMPLE | TARGET | CT VALUE | MAX FLUOR |
|---|---|---|---|
| Negative Control | Negative | — | — |
| Negative Control | Negative | — | — |
| Positive Control | Positive | 21.85 | 17.9 |
| Positive Control | Positive | 21.85 | 18.0 |
| A2-1 10 (fg) | Positive | 35.24 | 12.1 |
| A2-1 10 (fg) | Positive | 34.90 | 12.5 |
| A2-1 10 (fg) | Positive | 36.23 | 11.2 |
| A2-1 10 (fg) | Positive | 37.00 | 10.6 |
| A2-1 7 (fg) | Positive | 36.87 | 11.0 |
| A2-1 7 (fg) | Positive | 36.63 | 11.2 |
| A2-1 7 (fg) | Positive | 37.87 | 9.7 |
| A2-1 7 (fg) | Positive | 36.77 | 10.1 |
| A2-1 5 (fg) | Positive | 37.17 | 10.5 |
| A2-1 5 (fg) | Positive | 37.80 | 9.6 |
| A2-1 5 (fg) | Positive | 38.22 | 8.7 |
| A2-1 5 (fg) | Positive | 37.45 | 9.0 |
| A2-1 3 (fg) | Positive | 37.16 | 9.6 |
| A2-1 3 (fg) | Positive | 39.45 | 7.5 |

TABLE 5-continued

A2C REAL-TIM QPCR ASSAY

| SAMPLE | TARGET | CT VALUE | MAX FLUOR |
|---|---|---|---|
| A2-1 3 (fg) | Positive | 38.07 | 8.5 |
| A2-1 3 (fg) | Negative | — | — |
| A2-1 1 (fg) | Positive | 37.62 | 9.9 |
| A2-1 1 (fg) | Positive | 39.56 | 7.9 |
| A2-1 1 (fg) | Positive | 38.56 | 8.8 |
| A2-1 1 (fg) | Negative | — | — |

Figure 11:
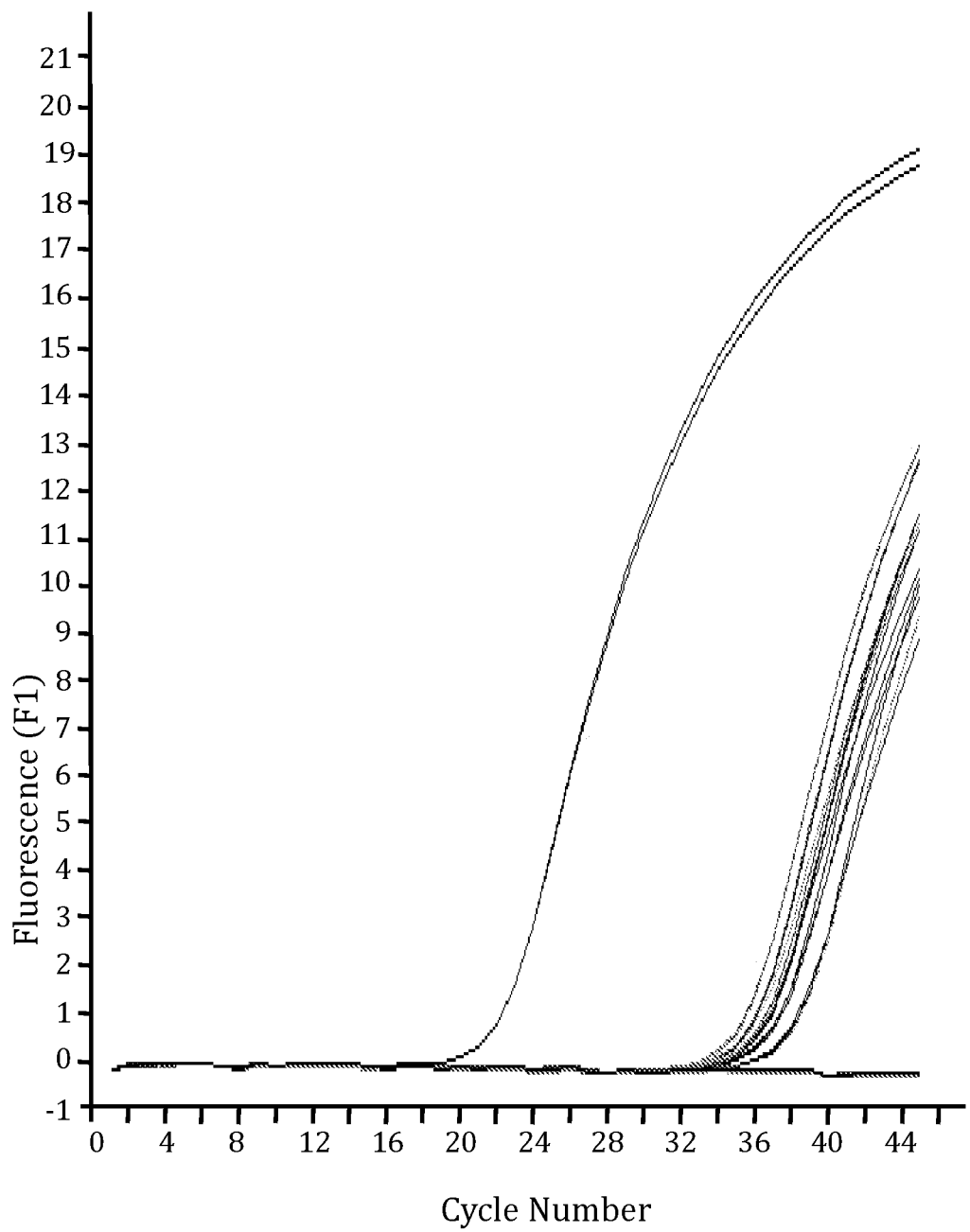

As illustrated in FIG. 11 and provided in Table 6, below, the B2 real-time qPCR assay was developed to detect *F. tularensis* subspecies *holarctica* (type B) strains. The limit of detection for the B2 real-time qPCR assay was determined to be less than 5 fg and greater than 3 fg of *F. tularensis* subspecies *holarctica* genomic DNA.

Optimized conditions for A2c assay (5 mM $MgCl_2$, 0.5 µM1V Forward primer, 0.25 µM Reverse primer, and 0.3 µM TaqMan probe), 20 µL total reaction volume: 9.4 µL sterile water, 2 µL 10×PCR Buffer, 2 µL $MgCl_2$ [50 mM], 2 µL 10×dNTP mix, 1 µL A2c Forward primer [10 µM], 0.5 µL A2c Reverse primer [10 µM], 1.5 µL A2c-P probe [4 µM], 0.5 µL BSA [10 mg/mL], 0.1 µL Platinum Taq [5 U/µL], and 1 µL DNA template.

TABLE 6

B2 REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control | Positive | 22.04 | 18.9 |
| Positive Control | Positive | 22.05 | 19.1 |
| B1-1 (10 fg) | Positive | 36.26 | 11.5 |
| B1-1 (10 fg) | Positive | 36.62 | 11.5 |
| B1-1 (10 fg) | Positive | 35.92 | 12.7 |
| B1-1 (10 fg) | Positive | 35.30 | 13.0 |
| B1-1 (7 fg) | Positive | 35.35 | 13.0 |
| B1-1 (7 fg) | Positive | 36.56 | 11.6 |
| B1-1 (7 fg) | Positive | 35.86 | 12.6 |
| B1-1 (7 fg) | Positive | 38.17 | 10.1 |
| B1-1 (5 fg) | Positive | 37.02 | 11.3 |
| B1-1 (5 fg) | Positive | 36.48 | 11.3 |
| B1-1 (5 fg) | Positive | 35.93 | 11.4 |
| B1-1 (5 fg) | Positive | 36.27 | 10.4 |
| B1-1 (3 fg) | Positive | 37.86 | 8.9 |
| B1-1 (3 fg) | Positive | 36.86 | 9.8 |
| B1-1 (3 fg) | Negative | — | — |
| B1-1 (3 fg) | Positive | 37.03 | 10.3 |
| B1-1 (1 fg) | Positive | 38.15 | 9.4 |
| B1-1 (1 fg) | Negative | — | — |
| B1-1 (1 fg) | Negative | — | — |
| B1-1 (1 fg) | Negative | — | — |

Figure 12:
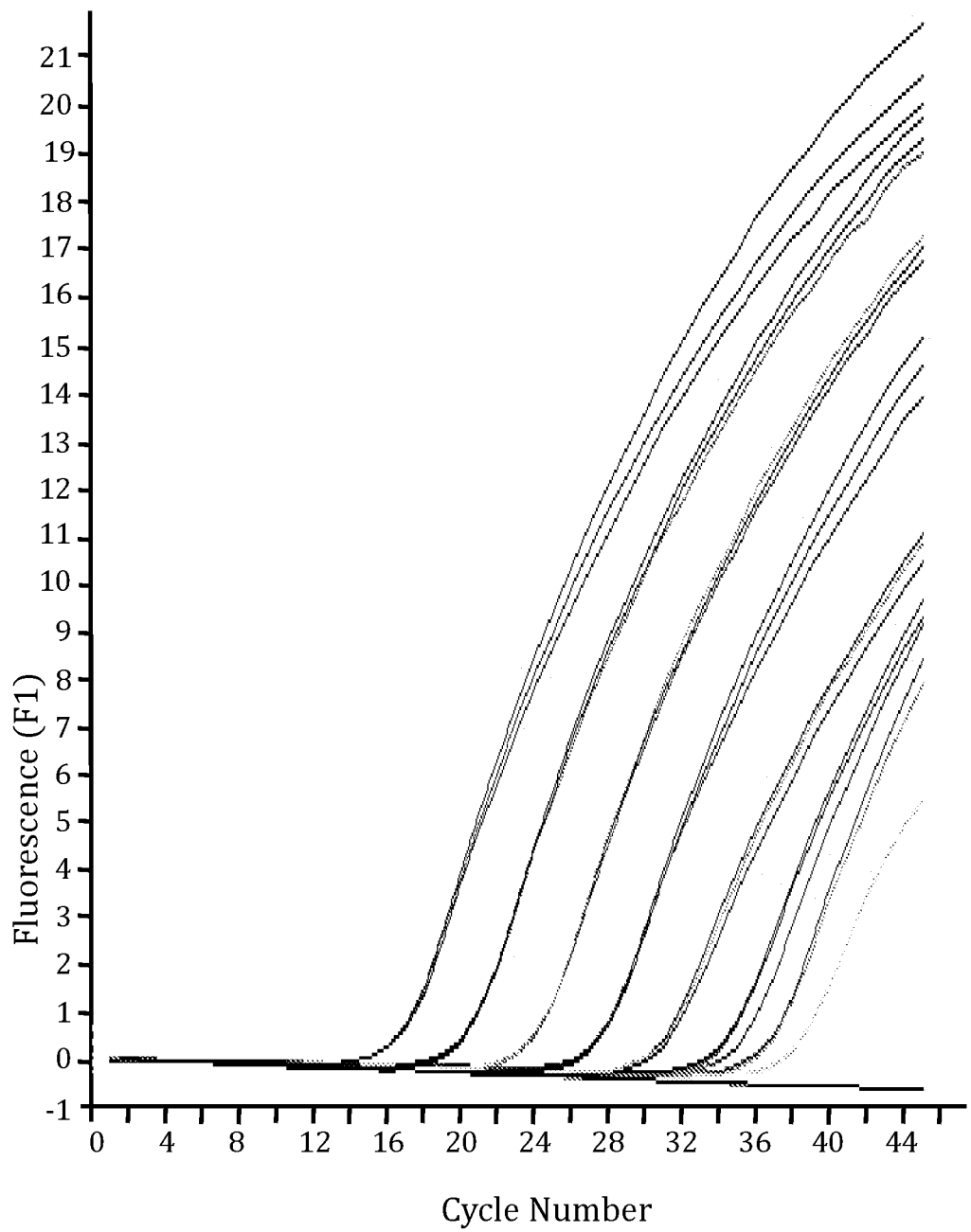
Figure 12A:
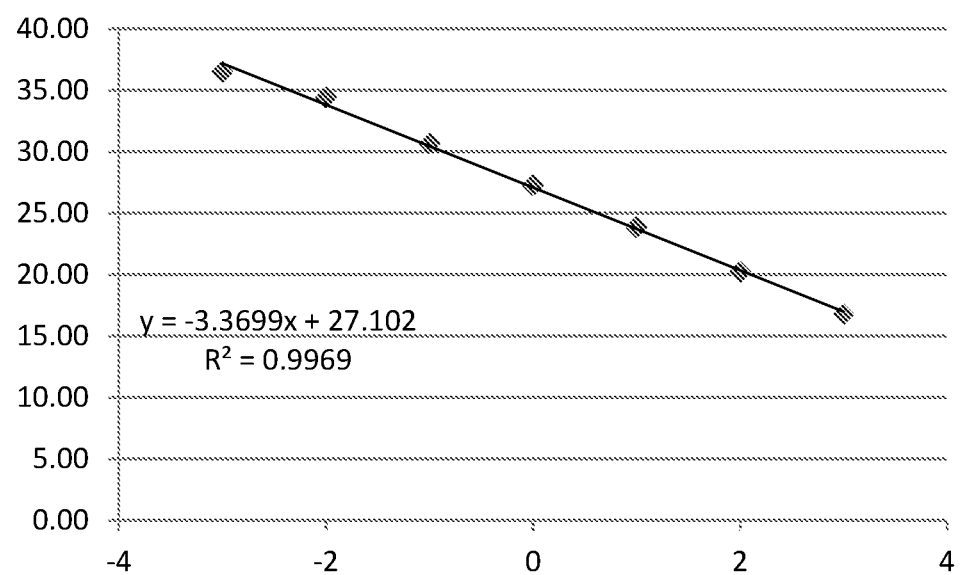
FIGS. 12A, 14A, 15A, 16A, 17A, 18A, and 19A are graphical representations of limits of detection of *F. tularensis* species, subspecies-, and subtypes using a singleplex assay.

As illustrated in FIG. 12 and provided in Table 7, below, the M3 real-time qPCR assay was developed to detect *F. tularensis* subspecies *mediasiatica* strains. FIG. 12A is a graphical representation of ten-fold dilutions of *F. tularensis* genomic DNA resulted in a linear standard curve. The limit of detection for the M3 real-time qPCR assay was determined to be 1 fg of *F. tularensis* genomic DNA, which is 1 genome equivalent.

Optimized conditions for B2 assay (5 mM $MgCl_2$, 0.5 µM Forward primer, 0.5 µM Reverse primer, and 0.2 µM TaqMan probe), 20 µL total reaction volume: 9.4 µL sterile water, 2 µL 10×PCR buffer, 2 µL $MgCl_2$ [50 mM], 2 µL 10×dNTP mix, 1 µL B2 Forward primer [10 µM], 1 µL B2 Reverse primer [10 µM], 1 µL B2-P probe [4 µM], 0.5 µL BSA [10 mg/mL], 0.1 µL Platinum Taq [5 U/µL], and 1 µL DNA template.

TABLE 7

M3 REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control [M-1 (1 ng)] | Positive | 16.74 | 20.0 |
| Positive Control [M-1 (1 ng)] | Positive | 16.80 | 21.8 |
| M1-1 (1 ng) | Positive | 16.78 | 20.7 |
| M1-1 (100 pg) | Positive | 20.24 | 19.9 |
| M1-1 (100 pg) | Positive | 20.21 | 19.3 |
| M1-1 (100 pg) | Positive | 20.22 | 19.1 |
| M1-1 (10 pg) | Positive | 23.89 | 17.4 |
| M1-1 (10 pg) | Positive | 23.88 | 17.2 |
| M1-1 (10 pg) | Positive | 23.85 | 16.9 |
| M1-1 (1 pg) | Positive | 27.38 | 15.3 |
| M1-1 (1 pg) | Positive | 27.29 | 14.7 |
| M1-1 (1 pg) | Positive | 27.12 | 14.0 |
| M1-1 (100 fg) | Positive | 30.69 | 10.9 |
| M1-1 (100 fg) | Positive | 30.80 | 10.5 |
| M1-1 (100 fg) | Positive | 30.52 | 11.0 |
| M1-1 (10 fg) | Positive | 34.13 | 9.6 |
| M1-1 (10 fg) | Positive | 35.04 | 9.3 |
| M1-1 (10 fg) | Positive | 34.07 | 9.4 |
| M1-1 (1 fg) | Positive | 36.49 | 8.0 |
| M1-1 (1 fg) | Positive | 36.51 | 8.4 |
| M1-1 (1 fg) | Positive | 37.62 | 5.6 |

Figure 13:
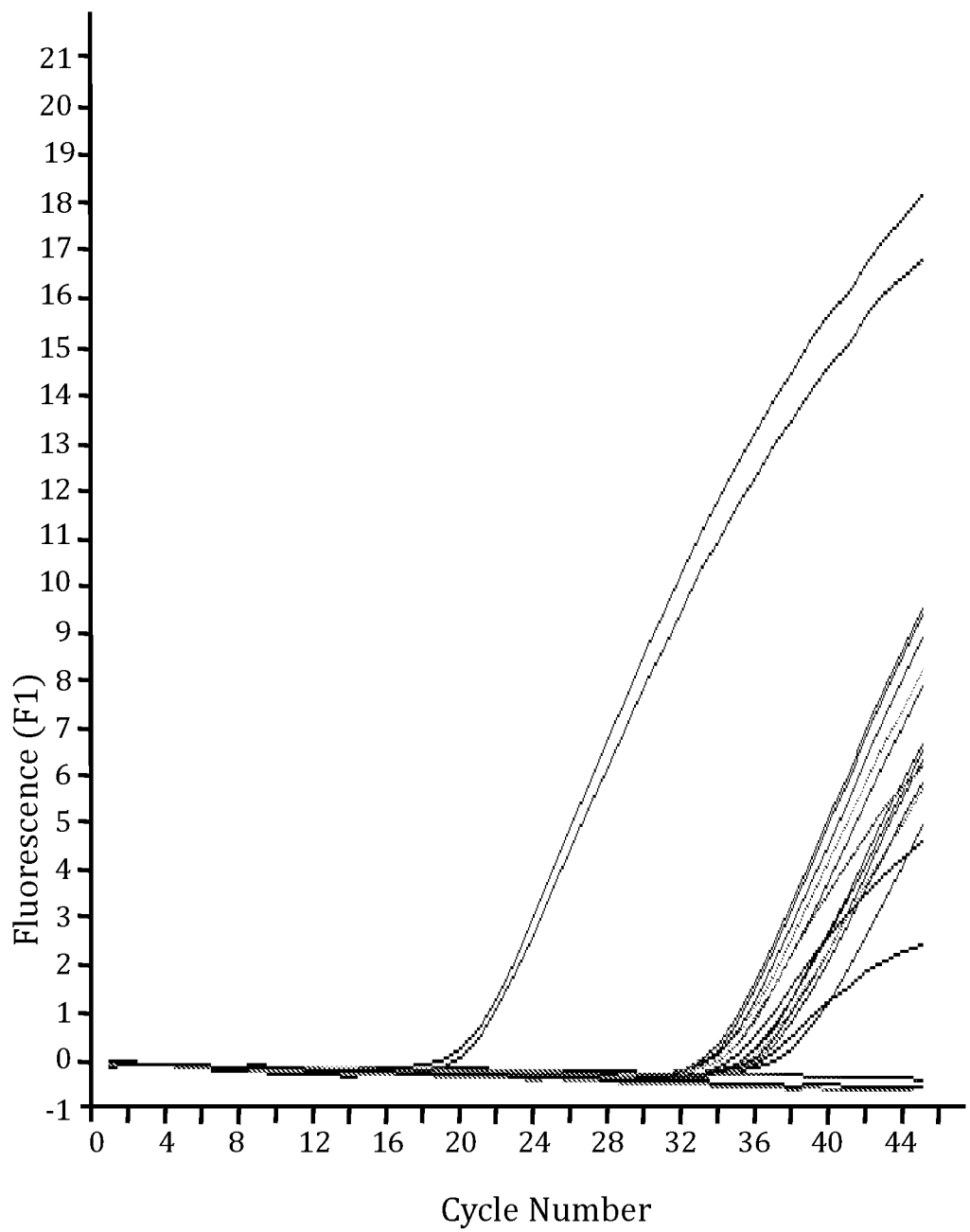

As illustrated in FIG. 13 and provided in Table 8, below, the N1 real-time qPCR assay was developed to detect *F. tularensis* subspecies *novicida* strains. The limit of detection for the N1 real-time qPCR assay was determined to be less than 3 fg and greater than 1 fg of *F. tularensis* subspecies *novicida* genomic DNA.

Optimized conditions for M3 assay (5 mM $MgCl_2$, 1 µM1V Forward primer, 0.75 µM Reverse primer, and 0.3 µM TaqMan probe), 20 µL total reaction volume: 7.4 µL sterile water, 2 µL 10×PCR Buffer, 2 µL $MgCl_2$ [50 mM], 2 µL 10×dNTP mix, 2 µL M3 Forward primer [10 µM], 1.5 µL M3 Reverse primer [10 µM], 1.5 µL M3-P probe [4 µM], 0.5 µL BSA [10 mg/mL], 0.1 µL Platinum Taq [5 U/µL], and 1 µL DNA template.

TABLE 8

N1 REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control | Positive | 20.68 | 16.9 |
| Positive Control | Positive | 20.70 | 18.2 |
| N (10 fg) | Positive | 33.90 | 9.5 |
| N (10 fg) | Positive | 34.04 | 9.4 |
| N (10 fg) | Positive | 34.30 | 9.0 |
| N (7 fg) | Positive | 34.31 | 6.3 |
| N (7 fg) | Positive | 34.41 | 8.3 |
| N (7 fg) | Positive | 34.42 | 4.7 |
| N (5 fg) | Positive | 34.88 | 7.9 |
| N (5 fg) | Positive | 35.84 | 6.5 |
| N (5 fg) | Positive | 35.94 | 6.6 |
| N (3 fg) | Positive | 36.57 | 5.9 |
| N (3 fg) | Positive | 36.02 | 5.8 |
| N (3 fg) | Positive | 36.43 | 6.4 |
| N (1 fg) | Positive | 35.46 | 2.5 |
| N (1 fg) | Positive | 38.04 | 5.0 |
| N (1 fg) | Negative | — | — |

Figure 14:
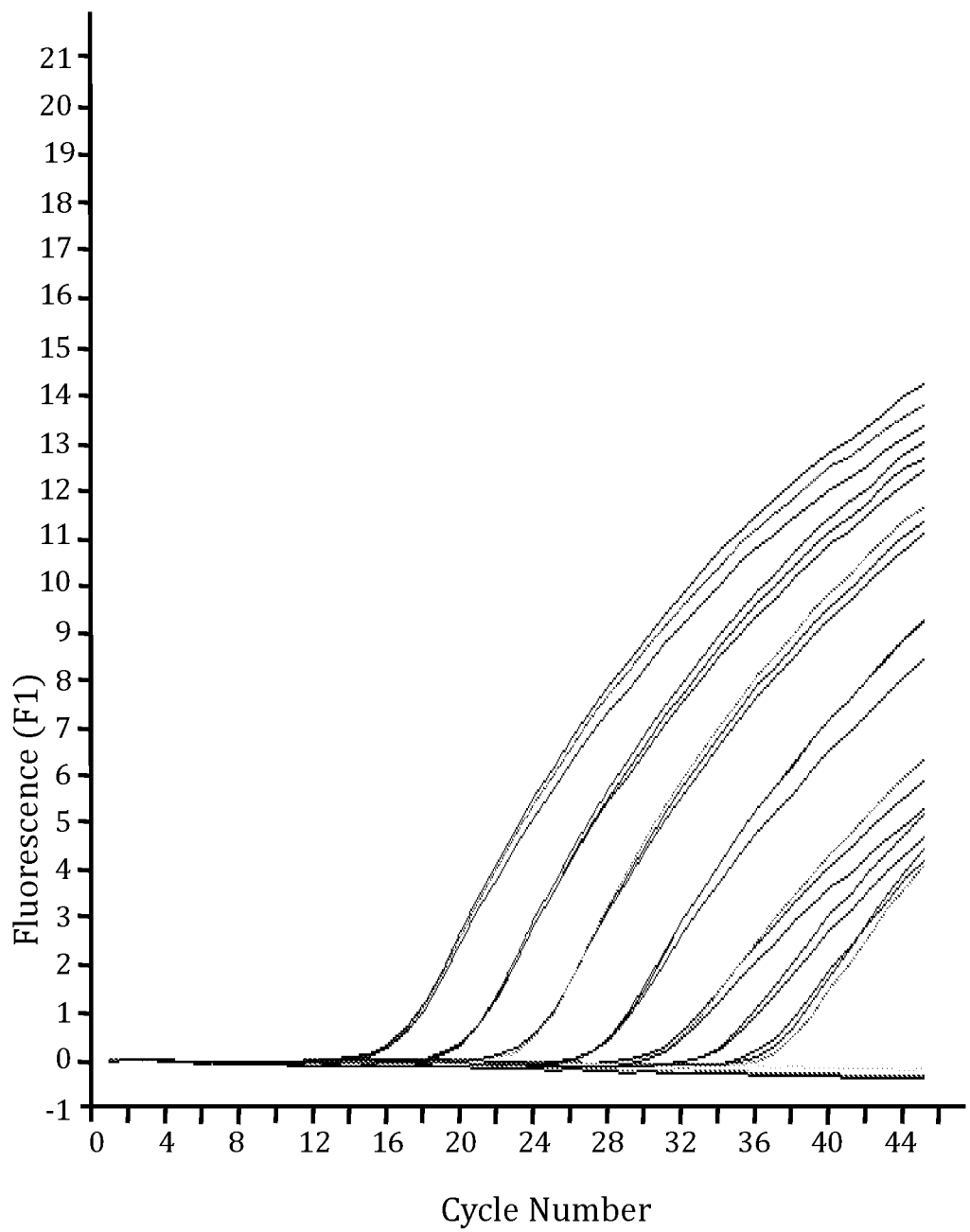
Figure 14A:
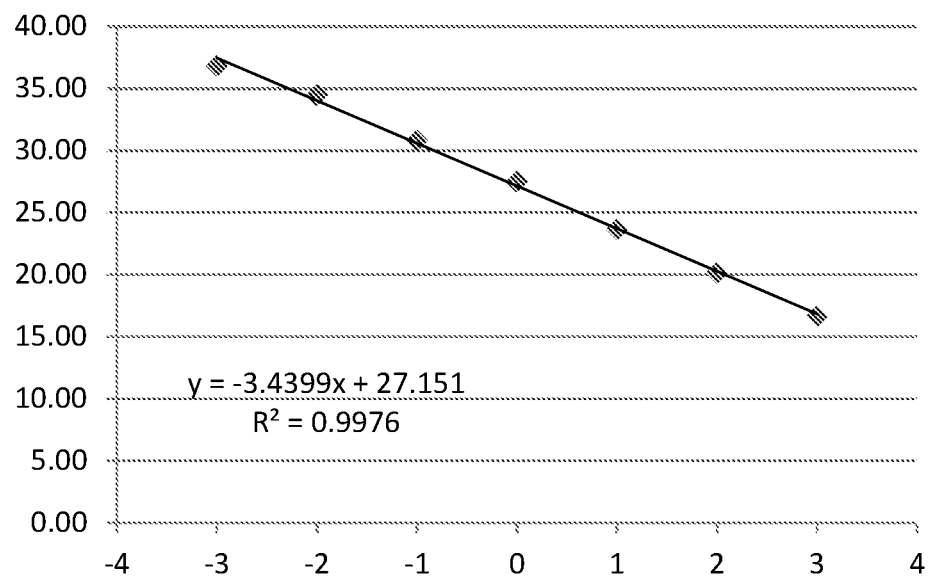

As illustrated in FIG. 14 and provided in Table 9, below, the 4Pan1 real-time qPCR assay was developed to detect all four *F. tularensis* subspecies, including avirulent subspecies *novicida*. FIG. 14A is a graphical representation of ten-fold dilutions of *F. tularensis* genomic DNA resulted in a linear standard curve.

Optimized conditions for N1 assay (5 mM MgCl$_2$, 0.5 µM Forward primer, 0.75 µM Reverse primer, and 0.4 µM TaqMan probe), 20 µL total reaction volume: 7.9 µL sterile water, 2 µL 10×PCR Buffer, 2 µL MgCl$_2$ [50 mM], 2 µL 10×dNTP mix, 1 µL N1 Forward primer [10 µM], 1.5 µL N1 Reverse primer [10 µM], 2 µL N1-P probe [4 µM], 0.5 µL BSA [10 mg/mL], 0.1 µL Platinum Taq [5 U/µL], and 1 µL DNA template.

TABLE 9

4PAN1 REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control [LVS (1 ng)] | Positive | 16.65 | 13.3 |
| Positive Control [LVS (1 ng)] | Positive | 16.65 | 14.0 |
| LVS (1 ng) | Positive | 16.68 | 13.7 |
| LVS (100 pg) | Positive | 20.12 | 12.4 |
| LVS (100 pg) | Positive | 20.17 | 12.5 |
| LVS (100 pg) | Positive | 20.14 | 13.0 |
| LVS (10 pg) | Positive | 23.71 | 11.6 |
| LVS (10 pg) | Positive | 23.65 | 11.3 |
| LVS (10 pg) | Positive | 23.59 | 11.1 |
| LVS (1 pg) | Positive | 27.66 | 9.3 |
| LVS (1 pg) | Positive | 27.41 | 9.8 |
| LVS (1 pg) | Positive | 27.41 | 8.5 |
| LVS (100 fg) | Positive | 31.02 | 6.4 |
| LVS (100 fg) | Positive | 30.68 | 5.9 |
| LVS (100 fg) | Positive | 30.75 | 5.3 |
| LVS (10 fg) | Positive | 33.69 | 4.7 |
| LVS (10 fg) | Positive | 33.62 | 5.2 |
| LVS (10 fg) | Positive | 36.06 | 4.2 |
| LVS (1 fg) | Positive | 36.97 | 4.1 |
| LVS (1 fg) | Positive | 36.70 | 4.4 |
| LVS (1 fg) | Negative | — | — |

Figure 15:
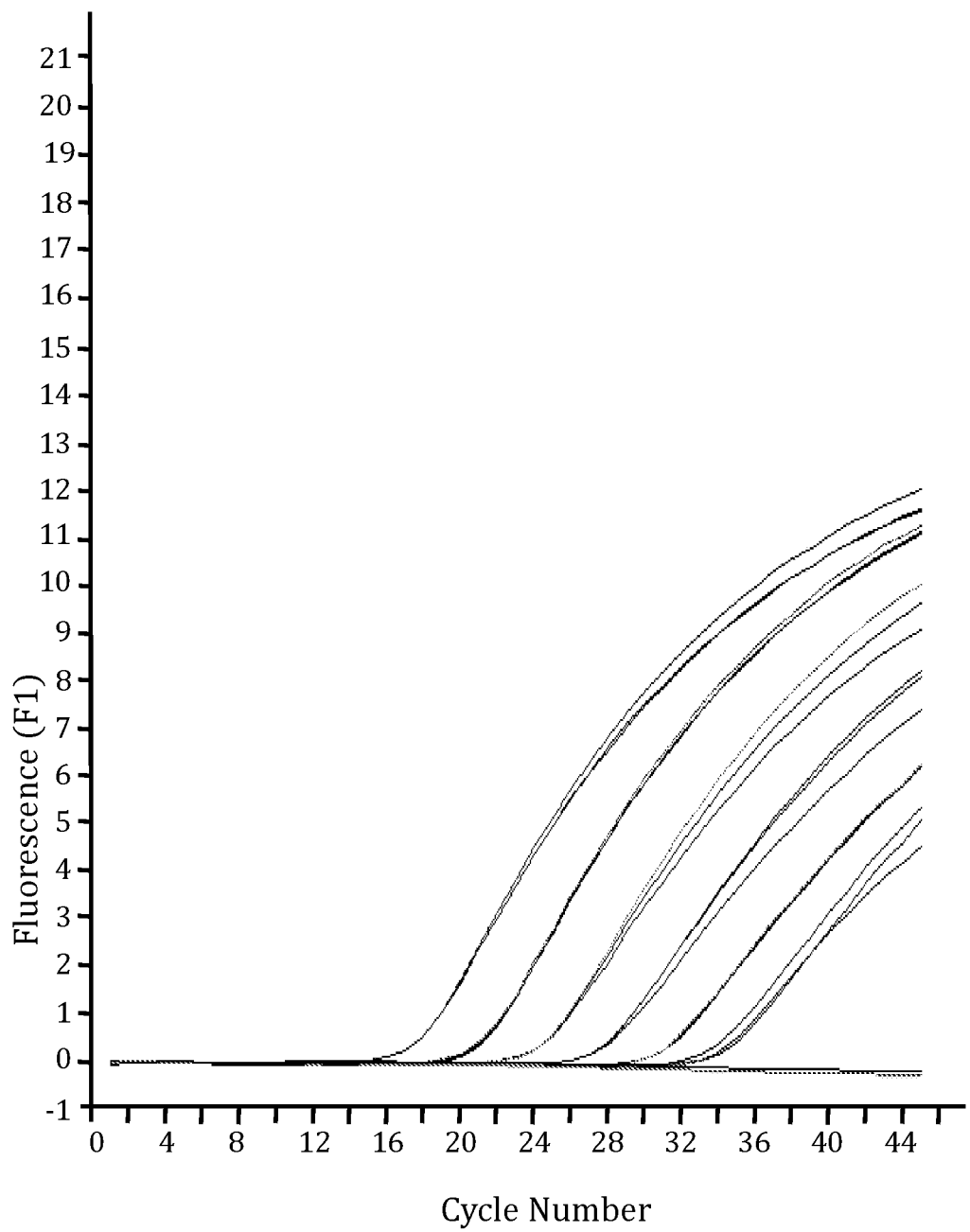
Figure 15A:
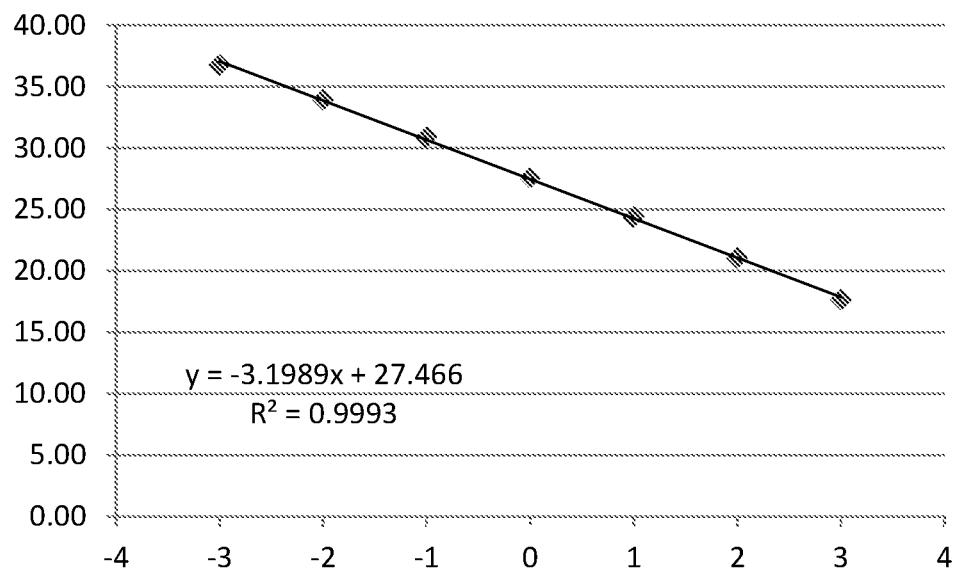

As illustrated in FIG. 15 and provided in Table 10, below, the 3Pan real-time qPCR assay was developed to detect the three virulent *F. tularensis* subspecies, and therefore, excludes avirulent subspecies *novicida*. FIG. 15A is a graphical representation of ten-fold dilutions of *F. tularensis* genomic DNA resulted in a linear standard curve.

TABLE 10

3PAN REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control [LVS (1000 pg)] | Positive | 17.65 | 11.6 |
| Positive Control [LVS (1000 pg)] | Positive | 17.66 | 11.6 |
| LVS (1000 pg) | Positive | 17.67 | 12.0 |
| LVS (100 pg) | Positive | 21.07 | 11.1 |
| LVS (100 pg) | Positive | 21.05 | 11.2 |
| LVS (100 pg) | Positive | 21.04 | 11.4 |
| LVS (10 pg) | Positive | 24.50 | 10.0 |
| LVS (10 pg) | Positive | 24.37 | 9.6 |
| LVS (10 pg) | Positive | 24.29 | 9.1 |
| LVS (1 pg) | Positive | 27.64 | 8.3 |
| LVS (1 pg) | Positive | 27.53 | 8.0 |
| LVS (1 pg) | Positive | 27.60 | 7.5 |
| LVS (100 fg) | Positive | 30.73 | 6.2 |
| LVS (100 fg) | Positive | 30.86 | 6.2 |
| LVS (100 fg) | Positive | 31.00 | 6.2 |
| LVS (10 fg) | Positive | 33.60 | 5.4 |
| LVS (10 fg) | Positive | 34.36 | 5.1 |
| LVS (10 fg) | Positive | 33.89 | 4.6 |

Figure 16:
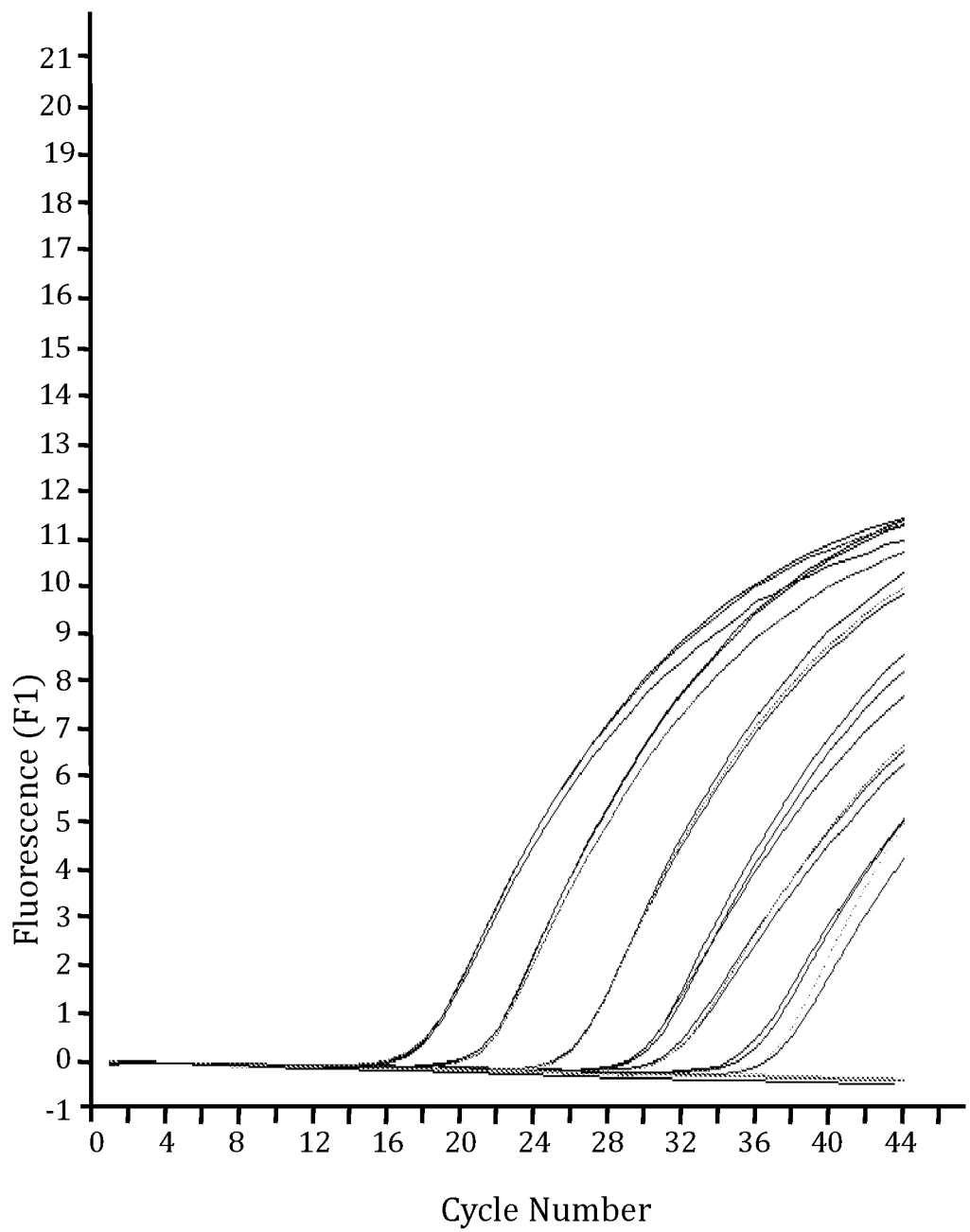
Figure 16A:
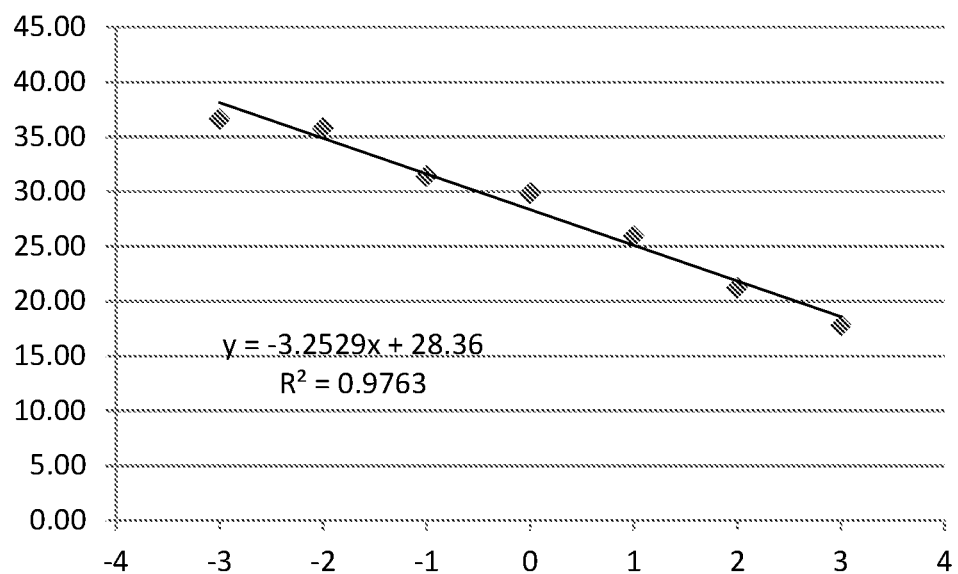

As illustrated in FIG. 16 and provided in Table 11, below, the A1d real-time qPCR assay was developed to detect *F. tularensis* subspecies *tularensis* subtype A.I. strains. FIG. 16A is a graphical representation of ten-fold dilutions of *F. tularensis* subspecies *tularensis* subtype A.I. genomic DNA resulted in a linear standard curve.

TABLE 11

A1D REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control [A1-1 (1 ng)] | Positive | 17.75 | 11.0 |
| Positive Control [A1-1 (1 ng)] | Positive | 17.76 | 11.5 |
| A1-1 (1 ng) | Positive | 17.79 | 11.4 |
| A1-1 (100 pg) | Positive | 21.21 | 11.5 |
| A1-1 (100 pg) | Positive | 21.23 | 11.4 |
| A1-1 (100 pg) | Positive | 21.21 | 10.7 |
| A1-1 (10 pg) | Positive | 25.92 | 10.0 |
| A1-1 (10 pg) | Positive | 25.96 | 10.4 |
| A1-1 (10 pg) | Positive | 25.88 | 9.9 |
| A1-1 (1 pg) | Positive | 30.00 | 8.3 |
| A1-1 (1 pg) | Positive | 29.83 | 8.6 |
| A1-1 (1 pg) | Positive | 29.70 | 7.7 |
| A1-1 (100 fg) | Positive | 31.51 | 6.7 |
| A1-1 (100 fg) | Positive | 31.16 | 6.6 |
| A1-1 (100 fg) | Positive | 31.52 | 6.4 |
| A1-1 (10 fg) | Positive | 35.12 | 5.1 |
| A1-1 (10 fg) | Positive | 36.72 | 4.3 |
| A1-1 (10 fg) | Positive | 35.51 | 5.1 |
| A1-1 (1 fg) | Negative | — | — |
| A1-1 (1 fg) | Negative | — | — |
| A1-1 (1 fg) | Positive | 36.59 | 5.0 |

Figure 17:
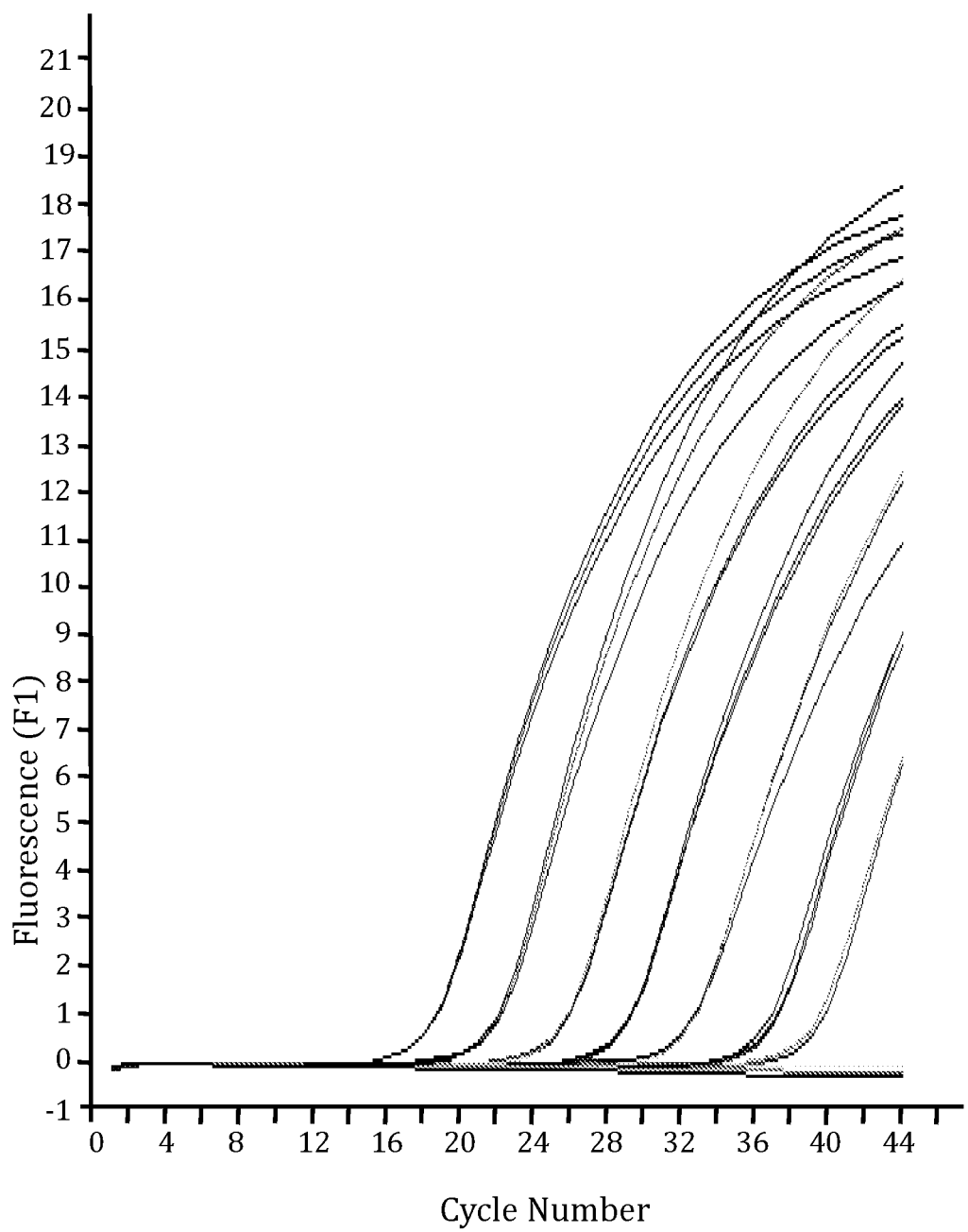
Figure 17A:
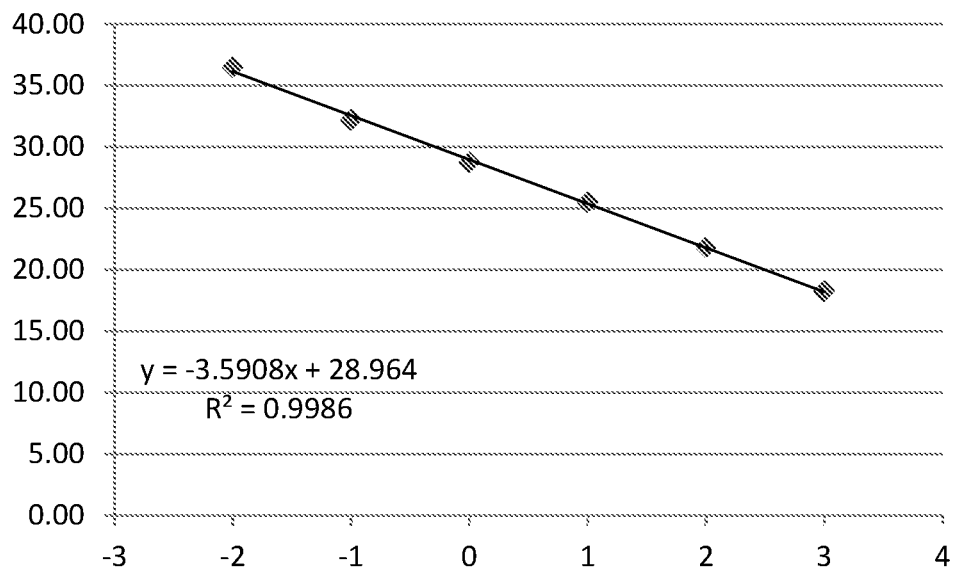

As illustrated in FIG. 17 and provided in Table 12, below, the A2c real-time qPCR assay was developed to detect *F. tularensis* subspecies *tularensis* subtype A.II strains. FIG. 17A is a graphical representation of ten-fold dilutions of *F. tularensis* subspecies *tularensis* subtype A.II genomic DNA resulted in a linear standard curve.

TABLE 12

A2C REAL-TIMEPQCR ASSAY

| SAMPLE | TARGET | CT VALUE | MAX FLUOR |
|---|---|---|---|
| Negative Control | Negative | — | — |
| Negative Control | Negative | — | — |
| Positive Control [A2-1 (1 ng)] | Positive | 18.24 | 17.9 |
| Positive Control [A2-1 (1 ng)] | Positive | 18.25 | 17.0 |
| A2-1 (1 ng) | Positive | 18.25 | 17.4 |
| A2-1 (100 pg) | Positive | 21.80 | 16.5 |
| A2-1 (100 pg) | Positive | 21.82 | 18.5 |

TABLE 12-continued

A2C REAL-TIME PQCR ASSAY

| SAMPLE | TARGET | CT VALUE | MAX FLUOR |
|---|---|---|---|
| A2-1 (100 pg) | Positive | 21.82 | 17.6 |
| A2-1 (10 pg) | Positive | 25.51 | 16.5 |
| A2-1 (10 pg) | Positive | 25.49 | 15.2 |
| A2-1 (10 pg) | Positive | 253.49 | 15.5 |
| A2-1 (1 pg) | Positive | 28.76 | 14.0 |
| A2-1 (1 pg) | Positive | 28.80 | 14.8 |
| A2-1 (1 pg) | Positive | 28.70 | 13.9 |
| A2-1 (100 fg) | Positive | 32.27 | 12.4 |
| A2-1 (100 fg) | Positive | 32.25 | 12.3 |
| A2-1 (100 fg) | Positive | 32.09 | 11.0 |
| A2-1 (10 fg) | Positive | 36.16 | 9.1 |
| A2-1 (10 fg) | Positive | 36.65 | 9.0 |
| A2-1 (10 fg) | Positive | 36.68 | 8.7 |
| A2-1 (1 fg) | Negative | — | — |
| A2-1 (1 fg) | Negative | — | — |
| A2-1 (1 fg) | Negative | — | — |

Figure 18:
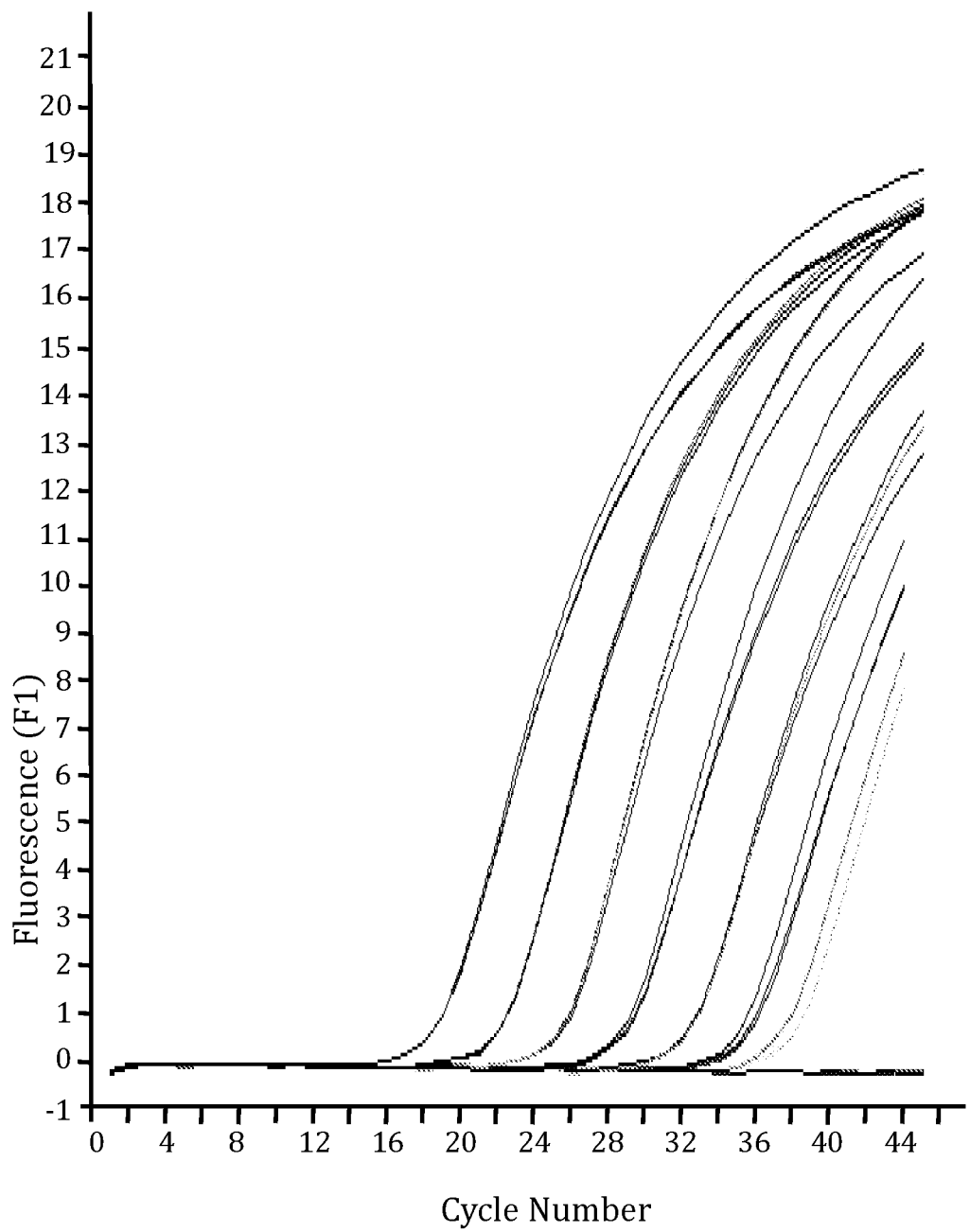
Figure 18A:
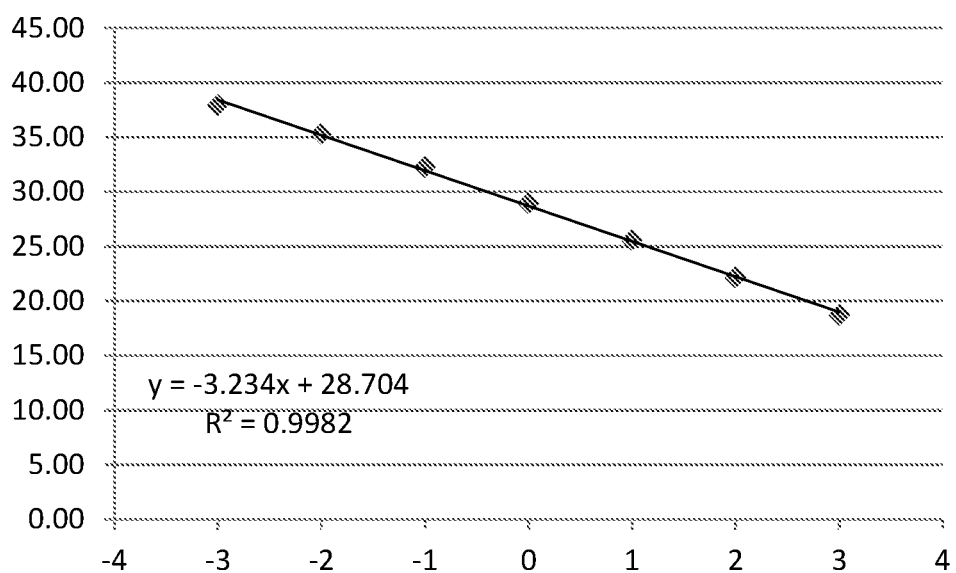

As illustrated in FIG. 18 and provided in Table 13, below, the B32 real-time qPCR assay was developed to detect *F. tularensis* subspecies *holarctica* (type B) strains. FIG. 18A is a graphical representation of ten-fold dilutions of *F. tularensis* subspecies *holarctica* genomic DNA resulted in a linear standard curve.

TABLE 13

B2 REAL-TIME QPCR ASSAY

| SAMPLE | TARGET | CT VALUE | MAX FLUOR |
|---|---|---|---|
| Negative Control | Negative | — | — |
| Negative Control | Negative | — | — |
| Positive Control [B1-1 (1 ng)] | Positive | 18.74 | 18.7 |
| Positive Control [B1-1 (1 ng)] | Positive | 18.73 | 17.8 |
| B1-1 (1 ng) | Positive | 18.74 | 17.9 |
| B1-1 (100 pg) | Positive | 22.17 | 17.9 |
| B1-1 (100 pg) | Positive | 22.17 | 18.0 |
| B1-1 (100 pg) | Positive | 22.15 | 18.0 |
| B1-1 (10 pg) | Positive | 25.58 | 17.9 |
| B1-1 (10 pg) | Positive | 25.56 | 17.9 |
| B1-1 (10 pg) | Positive | 25.59 | 17.0 |
| B1-1 (1 pg) | Positive | 29.01 | 15.0 |
| B1-1 (1 pg) | Positive | 28.88 | 16.4 |
| B1-1 (1 pg) | Positive | 28.94 | 14.9 |
| B1-1 (100 fg) | Positive | 32.34 | 13.3 |
| B1-1 (100 fg) | Positive | 32.30 | 13.6 |
| B1-1 (100 fg) | Positive | 32.18 | 12.7 |
| B1-1 (10 fg) | Positive | 35.01 | 11.0 |
| B1-1 (10 fg) | Positive | 35.36 | 9.9 |
| B1-1 (10 fg) | Positive | 35.58 | 10.0 |
| B1-1 (1 fg) | Positive | 37.33 | 8.5 |
| B1-1 (1 fg) | Negative | — | — |
| B1-1 (1 fg) | Positive | 38.51 | 7.8 |

Figure 19:
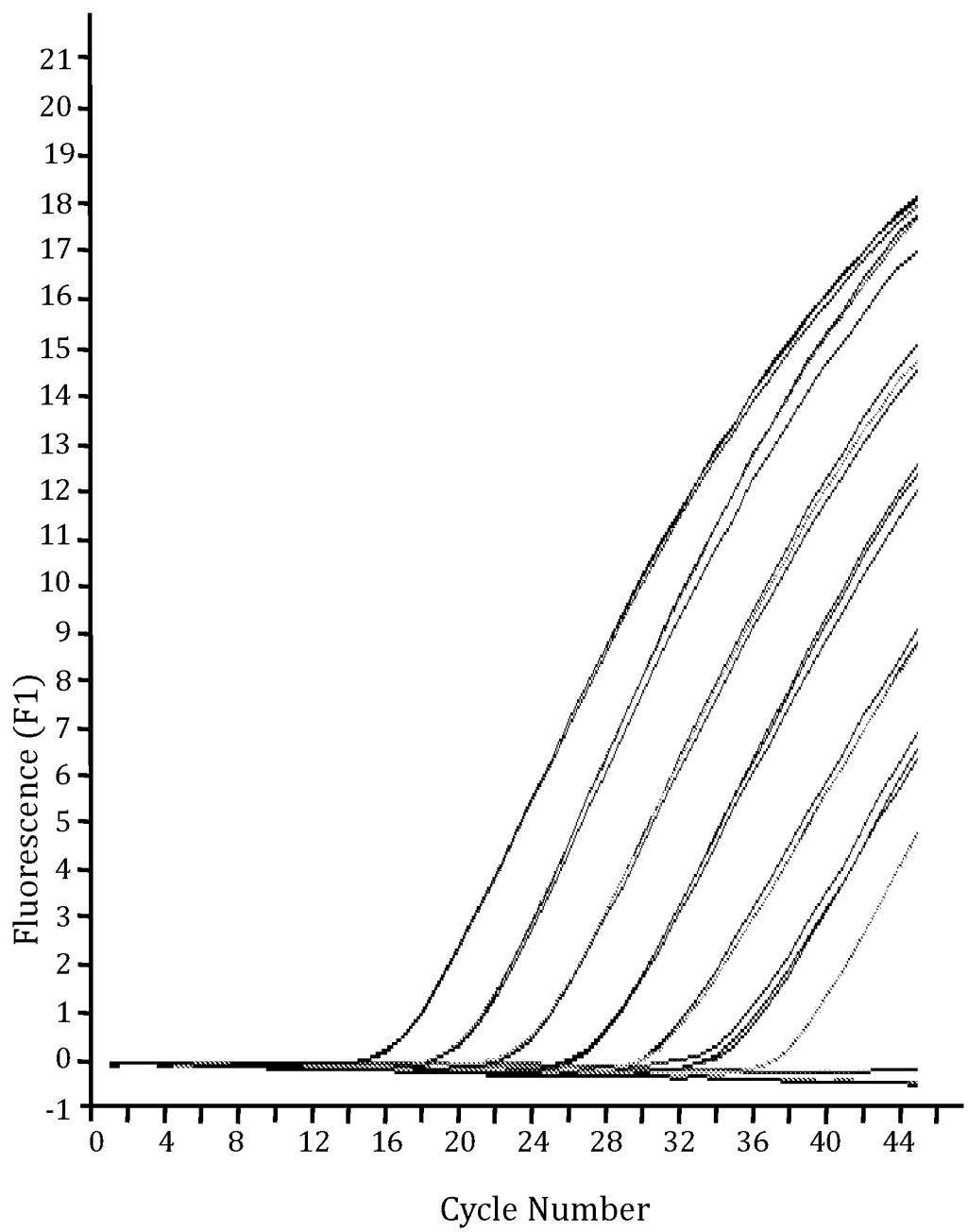
Figure 19A:
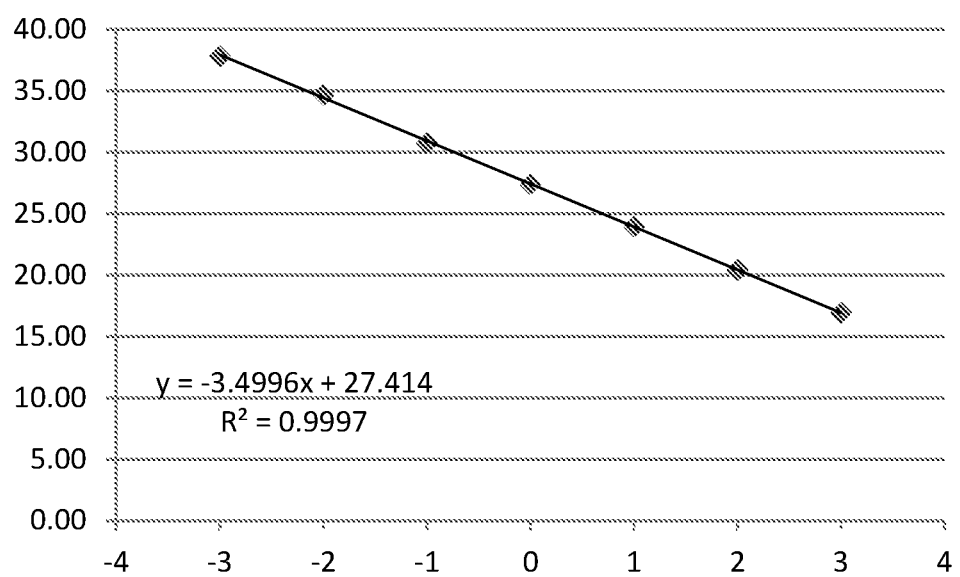

As illustrated in FIG. 19 and provided in Table 14, below, the N1 real-time qPCR assay was developed to detect *F. tularensis* subspecies *novicida* strains. FIG. 19A is a graphical representation of ten-fold dilutions of *F. tularensis* subspecies *novicida* genomic DNA resulted in a linear standard curve.

TABLE 14

N1 REAL-TIME QPCR ASSAY

| Sample | Target | Ct Value | Max Fluor |
|---|---|---|---|
| Negative Control | Negative | — | — |
| Negative Control | Negative | — | — |
| Positive Control (N 1 ng) | Positive | 16.92 | 18.1 |
| Positive Control (N 1 ng) | Positive | 16.92 | 18.1 |
| N (1 ng) | Positive | 16.92 | 17.9 |
| N (100 pg) | Positive | 20.40 | 17.0 |
| N (100 pg) | Positive | 20.41 | 17.7 |
| N (100 pg) | Positive | 20.44 | 17.6 |
| N (10 pg) | Positive | 24.02 | 14.6 |
| N (10 pg) | Positive | 23.94 | 15.0 |
| N (10 pg) | Positive | 23.88 | 14.5 |
| N (1 pg) | Positive | 27.40 | 12.3 |
| N (1 pg) | Positive | 27.45 | 12.5 |
| N (1 pg) | Positive | 27.32 | 11.9 |
| N (100 fg) | Positive | 30.87 | 8.7 |
| N (100 fg) | Positive | 30.48 | 9.0 |
| N (100 fg) | Positive | 30.86 | 8.6 |
| N (10 fg) | Positive | 34.47 | 6.4 |
| N (10 fg) | Positive | 34.46 | 6.9 |
| N (10 fg) | Positive | 35.07 | 6.5 |
| N (1 fg) | Positive | 37.82 | 4.8 |
| N (1 fg) | Negative | — | — |
| N (1 fg) | Negative | — | — |

Example 2

A multiplex "Tier 1" real-time qPCR assay was developed to detect all bacteria (universal 16S rDNA U16S target), all four *F. tularensis* subspecies including avirulent *novicida* (4Pan1 target), all three *F. tularensis* subspecies excluding avirulent *novicida* (3Pan target), and the most virulent *F. tularensis* strains, specifically subtype A.I. strains (A1d target). Assessment of the limit of detection (LOD) for each of the targets in the "Tier 1" multiplex real-time qPCR assay on the 7500 Fast Dx cycler showed that the LOD was greater than 50 fg and less than 30 fg for the 16S rDNA (U16S) target, less than 10 fg to greater than 1 fg for the 4Pan1 target, less than 30 fg to greater than 10 fg for the 3Pan target, and less than 30 fg to greater than 10 fg for the A1d target with *F. tularensis* subspecies *tularensis* subtype A.I. genomic DNA.

The LOD for 16S rDNA endogenous internal control in the multiplex qPCR assays ranged from 50 fg to 100 fg on the ABI 7500 Fast Dx (Applied Biosystems) and 3M Integrated (Focus Diagnostics) platforms. Ten-fold dilutions of *F. tularensis* subspecies *tularensis* subtype A.I genomic DNA resulted in a linear standard curve for all four targets, specifically the universal 16S rDNA (U16S), 4Pan1, 3Pan, and A1d, in the multiplex "Tier 1" real-time qPCR assay.

Figure 20A:
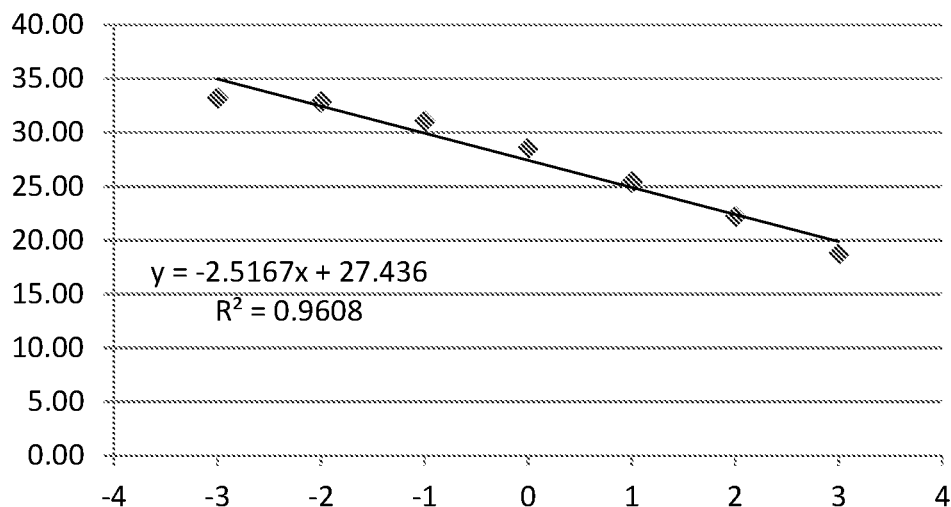
FIGS. 20A-20D are linear standard curves for four targets, namely, 16S rDNA, 4Pan1, 3Pan, and A1d, respectively, using a multiplex Tier 1 real-time qPCR assay. The "Tier 1" multiplex assay determines the presence of viable or nonviable (i) bacteria by the inclusion of the 16S rDNA primer and probe set; (ii) *F. tularensis* species by inclusion of the 4Pan1 primer and probe set; (iii) *F. tularensis* subspecies *tularensis* (type A), *holarctica* (type B), and *mediasiatica* by the inclusion of the 3Pan primer and probe set) and (iv) *F. tularensis* subspecies *tularensis* (type A) subtype A.I by inclusion of the A1d primer and probe set.
Figure 20B:
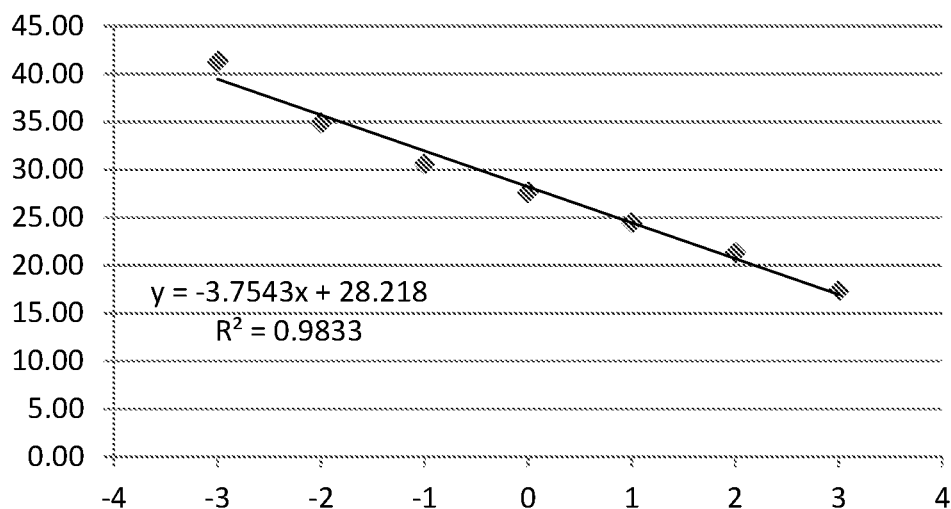
Figure 20C:
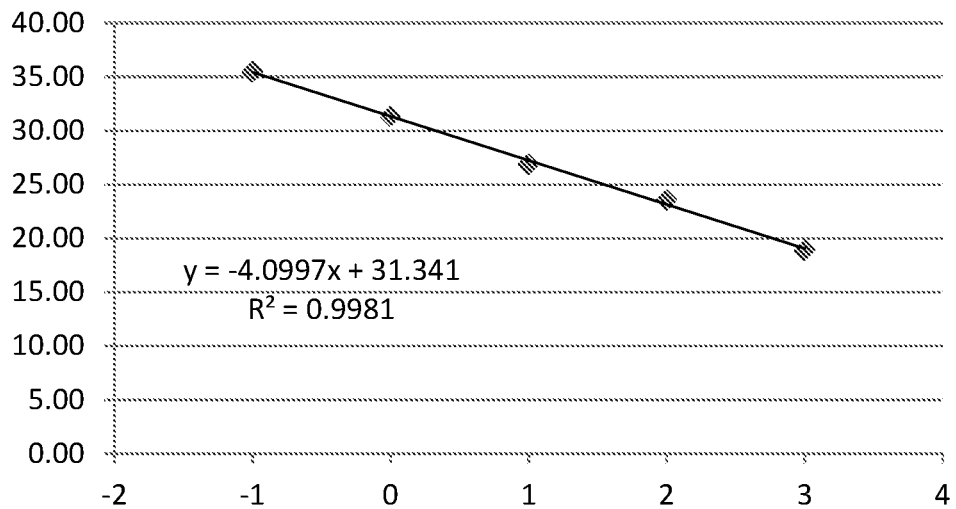
Figure 20D:
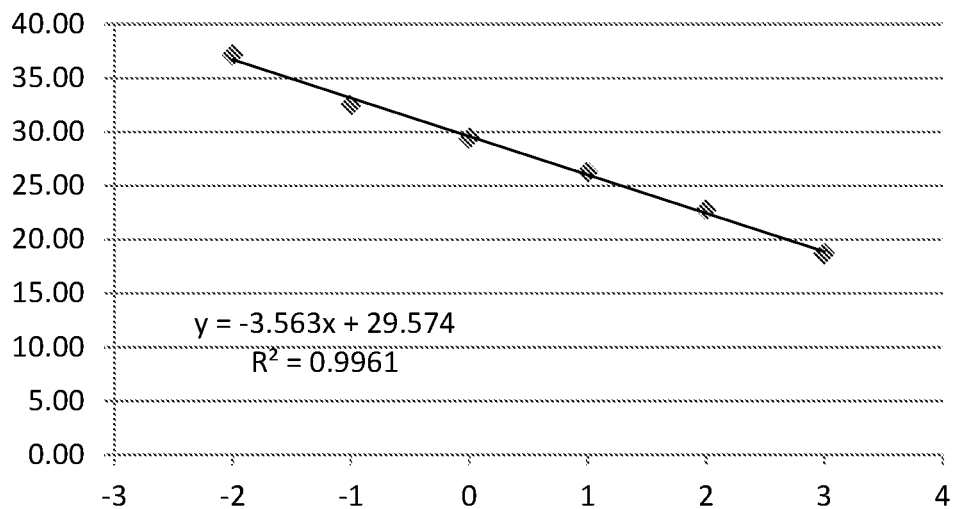

A multiplex "Tier 1" real-time qPCR assay was developed to detect all bacteria (universal 16S rDNA target U16S), all four *F. tularensis* subspecies including avirulent *novicida* (4Pan1 target), all three *F. tularensis* subspecies excluding avirulent *novicida* (3Pan target), and the most virulent *F. tularensis* strains, specifically subtype A.I strains (A1d target). Ten-fold dilutions of *F. tularensis* subspecies *tularensis* subtype A.I genomic DNA resulted in a linear standard curve for all four targets, specifically the universal 16S rDNA (U16S) (FIG. 20A), 4Pan1 (FIG. 20B), 3Pan (FIG. 20C), and A1d (FIG. 20D), in the multiplex "Tier 1" real-time qPCR assay. Assessment of the LOD for each of the targets in the "Tier 1" multiplex real-time qPCR assay on the 7500 Fast Dx cycler showed that the LOD was less than 100 fg and greater than 70 fg for the 16S rDNA target (U16S), less than 10 fg and greater than 1 fg for the 4Pan1 target, less than 30 fg and greater than 10 fg for the 3Pan target, and less than 30 fg and greater than 10 fg for the A1d target with *F. tularensis* subspecies *tularensis* subtype A.I genomic DNA.

TABLE 15

LOD FOR MULTIPLEX "TIER 1" REAL-TIME QPCR ASSAY

| | CT VALUE | | | |
|---|---|---|---|---|
| | U16S | 4PAN1 | 3PAN | A1D |
| Negative control | 32.46 | Negative | Negative | Negative |
| Negative control | 32.75 | Negative | Negative | Negative |
| Positive control [A1-1 (1 ng)] | 17.07 | 18.39 | 15.67 | 20.58 |
| Positive control [A1-1 (1 ng)] | 17.90 | 17.86 | 16.27 | 19.85 |
| A1-1 1 ng) | 17.62 | 18.43 | 16.20 | 20.45 |
| A1-1 100 pg) | 21.19 | 22.05 | 19.76 | 24.18 |
| A1-1 100 pg) | 21.02 | 22.00 | 19.79 | 24.21 |
| A1-1 100 pg) | 20.84 | 22.23 | 19.75 | 24.41 |
| A1-1 10 pg) | 24.23 | 25.52 | 23.42 | 27.32 |
| A1-1 10 pg) | 24.54 | 25.25 | 23.68 | 27.21 |
| A1-1 10 pg) | 24.38 | 25.08 | 23.61 | 27.26 |
| A1-1 1 pg) | 28.38 | 29.51 | 27.62 | 31.36 |
| A1-1 1 pg) | 27.37 | 28.81 | 27.04 | 30.96 |
| A1-1 1 pg) | 27.77 | 28.11 | 27.05 | 30.44 |
| A1-1 100 fg) | 30.48 | 32.02 | 32.06 | 34.08 |
| A1-1 100 fg) | 31.13 | 31.98 | 31.20 | 33.85 |
| A1-1 100 fg) | 31.28 | 31.94 | 30.78 | 34.26 |
| A1-1 70 fg) | 30.80 | 32.47 | 31.98 | 34.77 |
| A1-1 70 fg) | 31.49 | 34.59 | 32.05 | 35.09 |
| A1-1 70 fg) | 31.71 | 33.64 | 31.83 | 35.34 |
| A1-1 50 fg) | 30.69 | 34.64 | 34.11 | 36.83 |
| A1-1 50 fg) | 31.10 | 34.08 | 33.35 | 38.40 |
| A1-1 50 fg) | 31.53 | 34.64 | 33.54 | 36.27 |
| A1-1 30 fg) | 32.26 | 35.48 | 36.48 | 39.23 |
| A1-1 30 fg) | 30.90 | 34.75 | 33.76 | 35.60 |
| A1-1 30 fg) | 31.21 | 34.73 | 34.19 | 39.28 |
| A1-1 10 fg) | 31.15 | 39.34 | >40 | >40 |
| A1-1 10 fg) | 32.18 | 37.53 | Negative | >40 |
| A1-1 10 fg) | 32.92 | 35.35 | 36.09 | Negative |
| A1-1 1 fg) | 32.82 | Negative | 38.82 | Negative |
| A1-1 1 fg) | 33.27 | Negative | 35.35 | Negative |
| A1-1 1 fg) | 32.45 | Negative | Negative | Negative |
| LOD (fg): | ~50 | ~10 | ~30 | ~30 |

TABLE 16

LOD FOR MULTIPLEX "TIER 1" REAL-TIME QPCR ASSAY

| | CT VALUE | | | |
|---|---|---|---|---|
| | U16S | 4PAN1 | 3PAN | A1D |
| Negative control | 33.03 | Negative | Negative | Negative |
| Negative control | 32.73 | Negative | Negative | Negative |
| Positive control [A1-1 (1 ng)] | 18.77 | 17.32 | 19.03 | 18.74 |
| Positive control [A1-1 (1 ng)] | 18.06 | 16.76 | 18.32 | 18.21 |
| A1-1 (1 ng) | 19.41 | 17.98 | 19.33 | 19.07 |
| A1-1 (100 pg) | 22.32 | 21.39 | 23.65 | 22.86 |
| A1-1 (100 pg) | 22.49 | 21.62 | 24.02 | 23.12 |
| A1-1 (100 pg) | 21.81 | 20.89 | 23.02 | 22.35 |
| A1-1 (10 pg) | 25.69 | 24.67 | 27.10 | 26.29 |
| A1-1 (10 pg) | 25.31 | 24.44 | 26.67 | 26.30 |
| A1-1 (10 pg) | 25.17 | 24.27 | 26.92 | 26.20 |
| A1-1 (1 pg) | 29.90 | 28.52 | 31.92 | 30.26 |
| A1-1 (1 pg) | 28.07 | 27.66 | 31.19 | 29.14 |
| A1-1 (1 pg) | 27.66 | 26.71 | 30.97 | 28.64 |
| A1-1 (100 fg) | 31.33 | 31.362 | 36.31 | 33.09 |
| A1-1 (100 fg) | 30.86 | 30.62 | 35.26 | 32.25 |
| A1-1 (100 fg) | 30.97 | 29.91 | 34.91 | 32.13 |
| A1-1 (70 fg) | 30.61 | 28.33 | 33.87 | 30.98 |
| A1-1 (70 fg) | 33.52 | 34.01 | 24.81 | 34.29 |

TABLE 16-continued

LOD FOR MULTIPLEX "TIER 1" REAL-TIME QPCR ASSAY

| | CT VALUE | | | |
|---|---|---|---|---|
| | U16S | 4PAN1 | 3PAN | A1D |
| A1-1 (70 fg) | 32.04 | 33.96 | 36.74 | 33.94 |
| A1-1 (50 fg) | 31.64 | 33.01 | 37.85 | 33.92 |
| A1-1 (50 fg) | 32.09 | 32.28 | 38.94 | 33.79 |
| A1-1 (50 fg) | 33.89 | 33.09 | 37.71 | 34.51 |
| A1-1 (30 fg) | 32.26 | 34.06 | 38.74 | 36.21 |
| A1-1 (30 fg) | 32.45 | 33.12 | 37.79 | 35.25 |
| A1-1 (30 fg) | 33.01 | 34.09 | 34.91 | 35.83 |
| A1-1 (10 fg) | 33.27 | 35.79 | Negative | 37.09 |
| A1-1 (10 fg) | 32.54 | 33.97 | 44.45 | 37.23 |
| A1-1 (10 fg) | 32.82 | 34.85 | 41.94 | 40.31 |
| A1-1 (1 fg) | 33.61 | 39.45 | Negative | Negative |
| A1-1 (1 fg) | 32.86 | 43.14 | Negative | Negative |
| A1-1 (1 fg) | 32.77 | 42.18 | Negative | 37.69 |
| LOD (fg): | ~100 | ~10 | ~30 | ~30 |

Figure 21A:
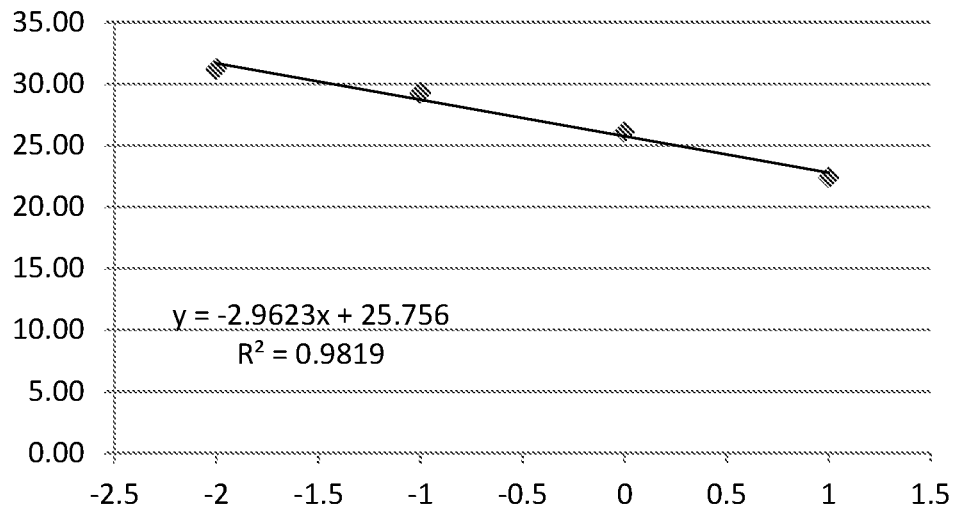
FIGS. 21A-21D are linear standard curves for four targets, namely, 16S rDNA, A2c, B2, and M3, respectively, using a multiplex Tier 2 real-time qPCR assay. The "Tier 2" multiplex assay determines the presence of viable and nonviable (i) bacterial by the inclusion of the 16S rDNA primer and probe set; (ii) *F. tularensis* subspecies *tularensis* (type A) subtype A.II; (iii) *F. tularensis* subspecies *holarctica* (type B); and (iv) *F. tularensis* subspecies *mediasiatica*.
Figure 21B:
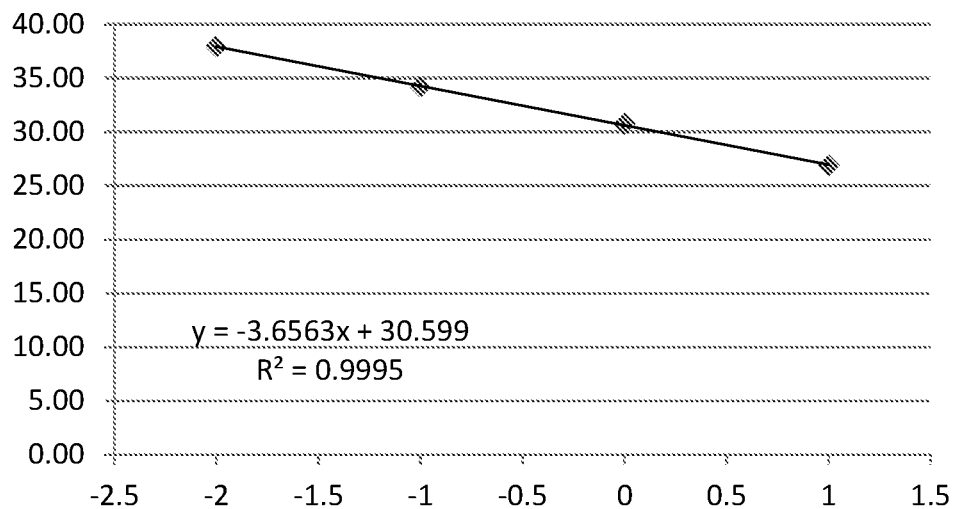
Figure 21C:
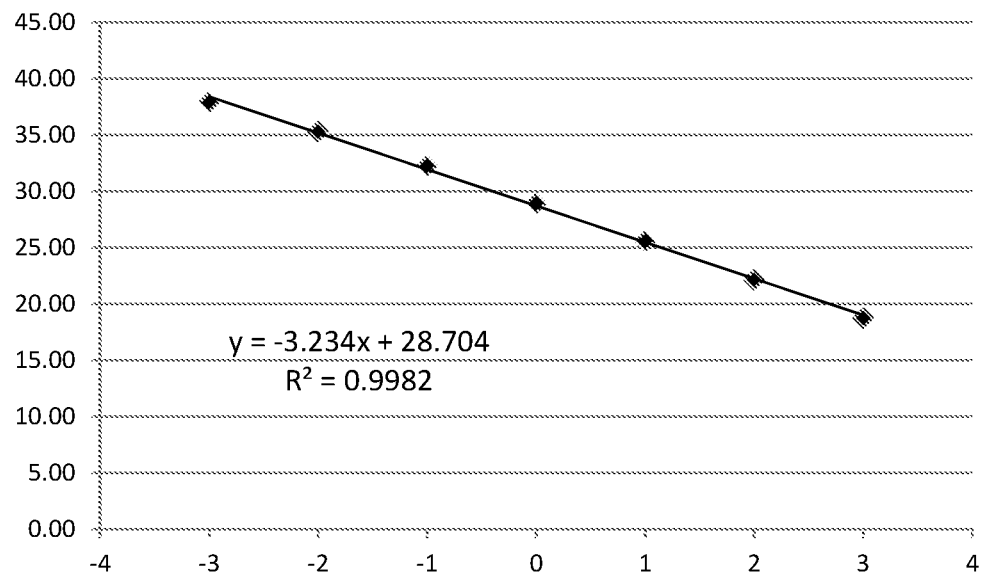
Figure 21D:
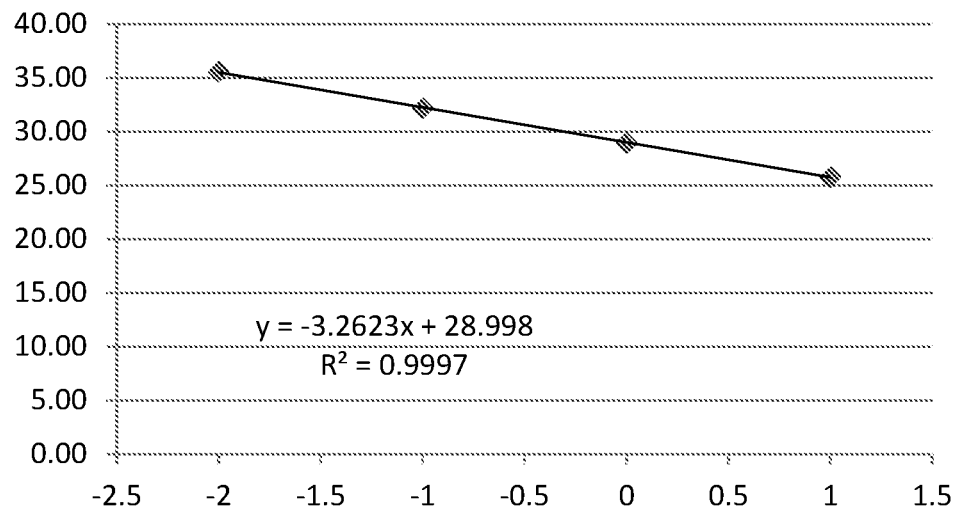

A multiplex "Tier 2" real-time PCR assay was developed to detect all bacteria (universal 16S rDNA target) and to differentiate *F. tularensis* subspecies *tularensis* subtype A.II (A2c target), *F. tularensis* subspecies *holarctica*, also referred to as type B (B2 target), and *F. tularensis* subspecies *mediasiatica* (M3 target). Ten-fold dilutions of the appropriate and designated *F. tularensis* genomic DNA resulted in a linear standard curve for all four targets, specifically the universal 16S rDNA (U16S) (FIG. 21A), A2c (FIG. 21B), B2 (FIG. 21C), and M3 (FIG. 21D), in the multiplex "Tier 2" real-time qPCR assay. The LOD for the multiplex "Tier 2" real-time qPCR assay targeting 16S rDNA (U16S) was determined to be 10 fg for subtype A.II, 30 fg for type B, and 50 fg for subspecies *mediasiatica*. The LOD for the multiplex "Tier 2" real-time qPCR assay targeting A2c was determined to be 10 fg for subtype A.II. The LOD for the multiplex "Tier 2" real-time qPCR assay targeting B2 was determined to be 30 fg for type B. The LOD for the multiplex "Tier 2" real-time qPCR assay targeting M3 was determined to be 10 fg for subspecies *mediasiatica*.

Optimized conditions for the Multiplex Tier 1 Real-Time PCR assay, 20 μL total reaction volume: 4.4 μL sterile water, 2 μL 10×PCR Buffer, 2 μL MgCl$_2$ [50 mM], 2 μL dNTP mix [2 mM each], 2 μL U16S 10× stock, 2 μL 4Pan1 10× stock, 2 μL 3Pan 10× stock, 2 μL A1d 10× stock, 0.5 μL BSA [10 mg/mL], 0.1 μL Platinum Taq [5 U/μL], and 1 μL DNA template.

The U16S 10× stock comprising (5 μM Forward Primer, 5 μM Reverse Primer, and 2 μM TaqMan Probe): 5 μL 16S-Forward primer [100 μM], 5 μL 16S-Reverse primer [100 μM], 2 μL Quasar670-16S-BHQ3 TaqMan probe [100 μM], and 88 μL TE buffer at pH 8.0.

The 4Pan1 10× stock comprising (5 μM Forward Primer, 7.5 μM Reverse Primer, and 4 μM TaqMan Probe): 5 μL 4Pan1-Forward primer [100 μM], 7.5 μL 4Pan1-Reverse primer [100 μM], 4 μL TxRd-4Pan1-BHQ2 TaqMan probe [100 μM], and 83.5 μL TE buffer at pH 8.0.

The 3Pan 10× stock comprising (5 μM Forward Primer, 5 μM Reverse Primer, and 5 μM TaqMan Probe): 5 μL 3Pan-Forward primer [100 μM], 5 μL 3Pan-Reverse primer [100 μM], 5 μL HEX-3Pan-BHQ1 TaqMan probe [100 μM], and 85 μL TE buffer at pH 8.0.

The A1d 10× stock comprising (5 μM Forward Primer, 5 μM Reverse Primer, and 2 μM TaqMan Probe): 5 μL A1d-Forward primer [100 μM], 5 μL A1d-Reverse primer [100 μM], 2 μL FAM-A1d-BHQ1 TaqMan probe [100 μM], and 88 μL TE buffer at pH 8.0.

TABLE 17

LOD FOR MULTIPLEX "TIER 2" REAL-TIME QPCR ASSAY

|  | CT VALUE | | | |
| --- | --- | --- | --- | --- |
|  | U16S | A2C | B2 | M3 |
| Negative control | 32.35 | Negative | Negative | Negative |
| Negative control | 32.46 | Negative | Negative | Negative |
| Positive control [A2-1 (10 pg)] | 22.50 | 27.06 | Negative | Negative |
| Positive control [A2-1 (10 pg)] | 22.25 | 26.72 | Negative | Negative |
| A2-1 (10 pg) | 22.41 | 26.85 | Negative | Negative |
| A2-1 (1 pg) | 26.02 | 30.57 | Negative | Negative |
| A2-1 (1 pg) | 26.15 | 30.98 | Negative | Negative |
| A2-1 (1 pg) | 26.11 | 30.67 | Negative | Negative |
| A2-1 (100 fg) | 29.60 | 34.45 | Negative | Negative |
| A2-1 (100 fg) | 28.82 | 33.88 | Negative | Negative |
| A2-1 (100 fg) | 29.38 | 34.19 | Negative | Negative |
| A2-1 (70 fg) | 30.20 | 35.16 | Negative | Negative |
| A2-1 (70 fg) | 30.51 | 35.49 | Negative | Negative |
| A2-1 (70 fg) | 30.43 | 34.81 | Negative | Negative |
| A2-1 (50 fg) | 30.66 | 35.31 | Negative | Negative |
| A2-1 (50 fg) | 30.57 | 35.28 | Negative | Negative |
| A2-1 (50 fg) | 30.42 | 35.64 | Negative | Negative |
| A2-1 (30 fg) | 30.60 | 36.15 | Negative | Negative |
| A2-1 (30 fg) | 30.97 | 36.34 | Negative | Negative |
| A2-1 (30 fg) | 31.07 | 36.58 | Negative | Negative |
| A2-1 (10 fg) | 31.66 | 38.56 | Negative | Negative |
| A2-1 (10 fg) | 30.62 | 37.84 | Negative | Negative |
| A2-1 (10 fg) | 31.33 | 37.36 | Negative | Negative |
| B1-1 (10 pg) | 22.70 | Negative | 28.57 | Negative |
| B1-1 (10 pg) | 22.41 | Negative | 28.34 | Negative |
| B1-1 (10 pg) | 22.59 | Negative | 28.51 | Negative |
| B1-1 (1 pg) | 26.00 | Negative | 31.88 | Negative |
| B1-1 (1 pg) | 26.02 | Negative | 31.68 | Negative |
| B1-1 (1 pg) | 25.80 | Negative | 31.56 | Negative |
| B1-1 (100 fg) | 29.62 | Negative | 35.03 | Negative |
| B1-1 (100 fg) | 29.27 | Negative | 35.55 | Negative |
| B1-1 (100 fg) | 29.64 | Negative | 34.97 | Negative |
| B1-1 (70 fg) | 29.79 | Negative | 35.32 | Negative |
| B1-1 (70 fg) | 29.31 | Negative | 36.01 | Negative |
| B1-1 (70 fg) | 29.86 | Negative | 36.16 | Negative |
| B1-1 (50 fg) | 31.00 | Negative | 36.29 | Negative |
| B1-1 (50 fg) | 30.33 | Negative | 36.40 | Negative |
| B1-1 (50 fg) | 31.04 | Negative | 36.42 | Negative |
| B1-1 (30 fg) | 30.96 | Negative | 36.75 | Negative |
| B1-1 (30 fg) | 31.76 | Negative | 37.36 | Negative |
| B1-1 (30 fg) | 31.05 | Negative | 36.81 | Negative |
| B1-1 (10 fg) | 32.31 | Negative | >40 | Negative |
| B1-1 (10 fg) | 31.82 | Negative | >40 | Negative |
| B1-1 (10 fg) | 32.44 | Negative | Negative | Negative |
| M1-1 (10 pg) | 23.26 | Negative | Negative | 26.16 |
| M1-1 (10 pg) | 22.76 | Negative | Negative | 25.76 |
| M1-1 (10 pg) | 22.71 | Negative | Negative | 25.46 |
| M1-1 (1 pg) | 26.68 | Negative | Negative | 28.82 |
| M1-1 (1 pg) | 26.30 | Negative | Negative | 29.03 |
| M1-1 (1 pg) | 26.44 | Negative | Negative | 29.01 |
| M1-1 (100 fg) | 29.46 | Negative | Negative | 32.35 |
| M1-1 (100 fg) | 29.78 | Negative | Negative | 32.35 |
| M1-1 (100 fg) | 29.18 | Negative | Negative | 31.86 |
| M1-1 (70 fg) | 32.70 | Negative | Negative | 34.35 |
| M1-1 (70 fg) | 30.94 | Negative | Negative | 33.05 |
| M1-1 (70 fg) | 30.49 | Negative | Negative | 33.02 |
| M1-1 (50 fg) | 30.69 | Negative | Negative | 33.57 |
| M1-1 (50 fg) | 30.91 | Negative | Negative | 33.77 |
| M1-1 (50 fg) | 31.45 | Negative | Negative | 33.43 |
| M1-1 (30 fg) | 32.30 | Negative | Negative | 34.89 |
| M1-1 (30 fg) | 32.43 | Negative | Negative | 34.87 |
| M1-1 (30 fg) | 31.76 | Negative | Negative | 34.34 |
| M1-1 (10 fg) | 32.59 | Negative | Negative | 36.29 |
| M1-1 (10 fg) | 31.78 | Negative | Negative | 35.69 |
| M1-1 (10 fg) | 31.97 | Negative | Negative | 34.80 |
| U16S LOD Subtype A.II (fg): | ~10 | N/A | N/A | N/A |
| U16S LOD Type B (fg): | ~30 | N/A | N/A | N/A |
| U16S LOD for mediasiatica (fg): | ~50 | N/A | N/A | N/A |
| A2c LOD Subtype A.II (fg): | N/A | ~10 | N/A | N/A |
| B2 LOD Type B (fg): | N/A | N/A | ~30 | N/A |
| M3 LOD mediasiatica (fg): | N/A | N/A | N/A | ~10 |

The specificities of the singleplex and multiplex *F. tularensis* species-, subspecies-, and subtype-specific qPCR assays were verified by evaluating an inclusivity test panel containing other bacterial species and closely related species (e.g., *F. philomiragia* and *F. persica*), as well as environmental ticks known to harbor *Francisella*-like bacteria (noted in Table 18, below).

TABLE 18

| *F. tularensis* Strain | Subspecies | Type or Subtype | Geographic Origin | Infected Host/Source | Year Isolated |
| --- | --- | --- | --- | --- | --- |
| **Schu S4 | *F. t. tularensis* | A.I | Ohio | Human | 1941 |
| NE-NPHL-061598 (UNMC) | *F. t. tularensis* | A.I | Nebraska | Human | 1998 |
| OK-OSU-98041035 | *F. t. tularensis* | A.I | Oklahoma | Cat | 1998 |
| NC-RADDL-48620-97 | *F. t. tularensis* | A.I | North Carolina | Rabbit | 1997 |
| AK-APHL_1100558 | *F. t. tularensis* | A.I | Arkansas | Hare | 2004 |
| MO-MPHL-D05 | *F. t. tularensis* | A.I | Missouri | Human | 2005 |
| NE-UNVDL-06F12348 | *F. t. tularensis* | A.I | Nebraska | Squirrel | 2007 |
| WY-WPHL-06F12348 | *F. t. tularensis* | A.I | Wyoming | Human | 2006 |
| NE-Child-090712 | *F. t. tularensis* | A.I | Nebraska | Human | 2012 |
| NE-UNLVDL-070213 | *F. t. tularensis* | A.I | Nebraska | Cat | 2013 |
| **WY96-3418-CDC | *F. t. tularensis* | A.II | Wyoming | Human | 1996 |
| WY-WSVL-00W4114 | *F. t. tularensis* | A.II | Wyoming | Prairie dog | 2000 |
| UT-UDHL-80402860 | *F. t. tularensis* | A.II | Wyoming | Human | 2004 |
| WY-WPHL-BT324 | *F. t. tularensis* | A.II | Wyoming | Human | 1996 |
| ATCC 6223 | *F. t. tularensis* | A.II | Unknown | Unknown | Unknown |
| WY-WPHL-03W10146 | *F. t. tularensis* | A.II | Wyoming | Human | 2003 |
| WY-WPHL-05W9954 | *F. t. tularensis* | A.II | Wyoming | Human | 2005 |
| WY-WPHL-06W9410 | *F. t. tularensis* | A.II | Wyoming | Human | 2006 |
| UT-UDHL-70102163 | *F. t. tularensis* | A.II | Utah | Human | 2001 |
| WY-WPHL-07F13554 | *F. t. tularensis* | A.II | Wyoming | Human | 2007 |
| **ATCC 29684 (LVS) | *F. t. holarctica* | B | Russia | Vole | Unknown |
| WY-WSVL-96194280 | *F. t. holarctica* | B | Wyoming | Rabbit | 1996 |
| WY-WSVL-9868529 | *F. t. holarctica* | B | Wyoming | Guinea pig | 1998 |

TABLE 18-continued

| F. tularensis Strain | Subspecies | Type or Subtype | Geographic Origin | Infected Host/Source | Year Isolated |
|---|---|---|---|---|---|
| WY-WSVL-OvineNC | F. t. holarctica | B | Wyoming | Sheep | Unknown |
| FR-LR | F. t. holarctica | B | France | Human | 1993 |
| NE-NPHL-061705 | F. t. holarctica | B | Nebraska | Human | 2005 |
| MO-MPHL-G05 | F. t. holarctica | B | Missouri | Human | 2005 |
| UT_UDH-70001092 | F. t. holarctica | B | Utah | Human | 2000 |
| NE-NPHL-072606 | F. t. holarctica | B | Nebraska | Human | 2006 |
| NE-Methodist-061113 | F. t. holarctica | B | Nebraska | Human | 2013 |
| **F. t. mediasiatica FSSC147 | F. t. mediasiatica | | Khazkhstan | Gerbil | 1965 |
| F. t. mediasiatica FSSC148 | F. t. mediasiatica | | Central Asia | Tick | 1982 |
| F. t. mediasiatica FSSC149 | F. t. mediasiatica | | Central Asia | Unknown | Unknown |
| **ATCC 15482 (U112) | F. t. novicida | | Utah | Water | 1951 |

**indicates reference strain

Optimized conditions for the Multiplex Tier 2 Real-Time PCR assay, 20 µL total reaction volume: 4.4 µL sterile water, 2 µL 10×PCR Buffer, 2 µL MgCl$_2$ [50 mM], 2 µL dNTP mix [2 mM each], 2 µL U16S 10× stock, 2 µL 4Pan1 10× stock, 2 µL 3Pan 10× stock, 2 µL A1d 10× stock, 0.5 µL BSA [10 mg/mL], 0.1 µL Platinum Taq [5 U/µL], and 1 µL DNA template.

The U16S 10× stock comprising (5 µM Forward Primer, 5 µM Reverse Primer, and 1 µM TaqMan Probe): 5 µL 16S-Forward primer [100 µM], 5 µL 16S-Reverse primer [100 µM], 1 µL Quasar670-16S-BHQ3 TaqMan probe [100 µM], and 89 µL TE buffer at pH 8.0.

The A2c 10× stock comprising (5 µM Forward Primer, 2.5 µM Reverse Primer, and 3 µM TaqMan Probe): 5 µL A2c-Forward primer [100 µM], 2.5 µL A2c-Reverse primer [100 µM], 3 µL FAM-A2c-BHQ1 TaqMan probe [100 µM], and 89.5 µL TE buffer at pH 8.0.

The B2 10× stock comprising (5 µM Forward Primer, 5 µM Reverse Primer, and 6 µM TaqMan Probe): 5 µL B2-Forward primer [100 µM], 5 µL B2-Reverse primer [100 µM], 6 µL TxRd-B2-BHQ2 TaqMan probe [100 µM], and 84 µL TE buffer at pH 8.0.

The M3 10× stock comprising (10 µM Forward Primer, 7.5 µM Reverse Primer, and 5 µM TaqMan Probe): 10 µL M3-Forward primer [100 µM], 7.5 µL M3-Reverse primer [100 µM], 5 µL JOE-M3-BHQ1 TaqMan probe [100 µM], and 77.5 µL TE buffer at pH 8.0

Currently, capability to rapidly differentiate among pathogens of operational significance in forward deployed areas is limited. To meet this gap, molecular-diagnostic testing, including singleplex subspecies differentiating real-time quantitative PCR (qPCR) assays, multiplex qPCR assays, and those that are sequence-based are proposed. These methodologies provide a set of tools to combat the threat of infection in a deployed scenario by allowing more accurate field detection of the F. tularensis pathogen. Consequently, method described herein according to embodiments of the present invention offer several improvements in the art of pathogen detection by providing a test that may be operated with PCR, qPCR, and sequencing technology. The method allows for the rapid deployment of robust assays with no foreknowledge requirement and provides unprecedented levels of organism detection.

The method can provide precise identification of even new and previously unobserved pathogens by their DNA sequence. Ultimately, such tools are an essential part of future etiological detection of disease and the epidemiology of pathogens in, but not limited to, the recruit and enlisted populations and emergency first responders, as well as the environment.

Because the four F. tularensis subspecies and the two type-A subtypes differ considerably in virulence, correctly identifying the stain type is critical for the appropriate response to a detection event. The PCR-based and sequence-based methods described herein are a vast improvement over other current assays, since this method can identify and differentiate the virulent F. tularensis strains from avirulent F. tularensis strains and other closely related nonpathogenic species, such as F. philomiragia, F. persica, and Francisella-like endosymbionts known to exist in ticks and other arthropod and insects (e.g., mosquitoes and deer flies). Thus the method as described according to the various embodiments herein (i) can differentiate the four F. tularensis subspecies and two type-A subtypes in PCR-based assays, real-time quantitative singleplex PCR assays, or real-time quantitative multiplex PCR assays without the need for a scoring matrix, (ii) can detect strain variation and is operable in a sequencing, PCR and/or real-time quantitative PCR based method, and (iii) is adaptable for the identification of emerging or novel pathogens of operational concern.

Methods according to the embodiments described herein enable a skilled operator of the JBAIDS, a fielded real-time quantitative PCR (qPCR) instrument, or other PCR-based platforms and sequencing devices to provide efficient and reliable subspeciation, subtyping, or both of F. tularensis with very low false-positive and false-negative rates (less than 2%). Embodiments of the method may comprise one or more multiplex assays or up to seven independent assays having one target each for speciation, subspeciation, subtyping, or a combination thereof.

All embodiments of the present invention provide no less than 95% accuracy of the identity of the F. tularensis subspecies or subspecies tularensis subtypes A.I and A.II. Sequencing-based assays may follow qPCR and provide the same or enhanced accuracy for subspeciation, subtyping, and strain identification.

Successful development of the sequence-based assay is important because unlike PCR, leveraging direct observation of DNA sequence is the most precise way to barcode the tested organisms. These sequences may be used to identify, track, or dismiss the source of the infectious agent.

Methods according to the various embodiments described herein offer a very high degree of precision in strain typing. Variants may be observed with considerably more granularity than other convention methods for F. tularensis via SNP profiling, closely related relatives, and other organisms. No less than 20 discreetly identifiable groups may be observed, which enables an operator to identify and track a particular pathogen release with great precision that is not attainable with PCR or qPCR alone.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A detection assay kit for detecting a presence of *Francisella tularensis* (*F. tularensis*) or *F. tularensis* nucleic acid, the kit comprising:
   a first plurality of primers comprising SEQ ID NO 4 and SEQ ID NO 5 and a first probe comprising a fluorescent reporter dye coupled to an initial 5'-nucleotide of SEQ ID NO 6.

2. The detection assay kit of claim 1, wherein the first probe further comprises:
   a quencher coupled to the initial 3'-nucleotide of SEQ ID NO 6.

3. The detection assay kit of claim 1, further comprising:
   a second plurality of primers comprising SEQ ID NO 1 and SEQ ID NO 2.

4. The detection assay kit of claim 3, further comprising:
   a second probe comprising a fluorescent reporter dye coupled to an initial 5'-nucleotide of SEQ ID NO 3.

5. The detection assay kit of claim 1, further comprising: reagents for a PCR process.

6. The detection assay kit of claim 4, wherein the second probe further comprises a quencher coupled to the initial 3'-nucleotide of SEQ ID NO 3.

7. The detection assay kit of claim 1, further comprising: reagents for a real time PCR process.

* * * * *